United States Patent

Nakajima et al.

Patent Number: 5,715,173
Date of Patent: Feb. 3, 1998

[54] CONCENTRATION CONTROLLING METHOD AND A SUBSTATE TREATING APPARATUS UTILIZING SAME

[75] Inventors: Kazuo Nakajima; Katsunori Tanaka; Nobutoshi Ogami, all of Shiga, Japan

[73] Assignee: Dainippon Screen Mfg. Co., Ltd., Kyoto, Japan

[21] Appl. No.: 490,830

[22] Filed: Jun. 15, 1995

[30] Foreign Application Priority Data

| Jun. 27, 1994 | [JP] | Japan | 6-168712 |
| Jul. 4, 1994 | [JP] | Japan | 6-176085 |
| Aug. 29, 1994 | [JP] | Japan | 6-228950 |
| Mar. 2, 1995 | [JP] | Japan | 7-070785 |

[51] Int. Cl.$^6$ ............................................. G01N 21/59
[52] U.S. Cl. ............... 364/500; 356/432; 356/435; 356/442; 356/319; 250/575; 359/127; 134/30
[58] Field of Search ............... 356/432, 435, 356/436, 440, 442, 445, 319; 250/575, 576, 226; 359/127; 134/30, 31; 364/500

[56] References Cited

U.S. PATENT DOCUMENTS

| 5,225,690 | 7/1993 | Sakai et al. | 250/561 |
| 5,288,333 | 2/1994 | Tanaka et al. | 134/31 |
| 5,422,703 | 6/1995 | Horie et al. | 356/445 |

FOREIGN PATENT DOCUMENTS

| 61-281532 | 12/1986 | Japan. |
| 62-8040 | 1/1987 | Japan. |
| 2-196946 | 8/1990 | Japan. |
| 5-74755 | 3/1993 | Japan. |
| 5-53241 | 7/1993 | Japan. |

*Primary Examiner*—Emanuel T. Voeltz
*Assistant Examiner*—Kamini Shah
*Attorney, Agent, or Firm*—Ostrolenk, Faber, Gerb & Soffen, LLP

[57] ABSTRACT

Calibration curve data is collected by measuring transmitted light intensities of a treating solvent while solvent temperature is varied. Also measured are a standard transmitted light intensity (transmitted light intensity of a standard treating solution prepared at a predetermined concentration and temperature) and a reference transmitted light intensity (transmitted light intensity of the solvent). Estimated transmitted light intensity of the solvent when its temperature is the same as that of the standard treating solution, is derived from the temperature of the standard treating solution and the calibration curve data stored. A correction factor is computed from a ratio between the reference transmitted light intensity and estimated transmitted light intensity. Then, transmittance of the standard treating solution (standard transmittance) is computed from the standard transmitted light intensity, reference transmitted light intensity and a correction factor. Subsequently, transmitted light intensity of a treating solution for actual use in treating substrates (sample transmitted light intensity) is measured. A sample transmittance of this treating solution is derived from the sample transmitted light intensity, reference transmitted light intensity and a correction factor. Concentration of the treating solution is controlled based on the standard and sample transmittance.

22 Claims, 16 Drawing Sheets

CONCENTRATION CONTROLLING METHOD AND A SUBSTATE TREATING APPARATUS UTILIZING SAME

BACKGROUND OF THE INVENTION (1) Field of the Invention

The present invention relates to concentration controlling methods for controlling the concentration of a treating solution for use in treatment of substrates, the concentration control being based on transmittance of the treating solution computed from a ratio between transmitted light intensity of the treating solution and transmitted light intensity of a solvent contained in the treating solution and maintained at a fixed temperature. The invention relates also to substrate treating apparatus utilizing such methods in cleaning, etching or otherwise treating semiconductor wafers, glass substrates for photomasks, glass substrates for liquid crystal displays, substrates for optical disks and the like.

(2) Description of the Related Art

Conventional substrate treating apparatus of the type noted above include an apparatus for cleaning substrates. To clean substrates such as semiconductor wafers, this substrate treating apparatus prepares a cleaning solution by mixing a chemical suited for the purpose with deionized water (solvent) in a predetermined ratio, and cleans substrates by immersing them in the cleaning solution. In many cases, the cleaning solution is heated, for example, to about 70° C. for use. The concentration of the cleaning solution is variable depending upon evaporation of the chemical and deionized water, and/or with other factors. The variations in the concentration of the cleaning solution makes it impossible to attain a desired clean condition of the substrates after a predetermined cleaning time. In the event of such variation, the concentration must be controlled to maintain a predetermined level. In a method of controlling the concentration of a treating solution such as a cleaning solution, transmittance of the treating solution is computed from a ratio between transmitted light intensity of the treating solution (sample transmitted light intensity) and transmitted light intensity of deionized water (reference transmitted light intensity) which serves as a standard or criterion, and the concentration of the treating solution is controlled based on this transmittance. According to this method, it is necessary to measure the transmittance of the treating solution in order to control the concentration thereof.

In a technique of measuring the transmittance, the transmitted light intensity of the treating solution is measured by using a flow cell mounted in a treating solution supply pipe through which the treating solution is supplied to the treating bath, and the transmitted light intensity of deionized water is measured by using a reference cell. The transmittance of the treating solution is calculated based on the ratio between the above intensities, using deionized water as a criterion.

However, as noted above, the cleaning solution is heated for use in cleaning substrates such as semiconductor wafers. On the other hand, the absorption coefficient of deionized water contained in the cleaning solution changes depending on the temperature thereof. The measured transmitted light intensity of the hot cleaning solution is measured as being higher than that measured at room temperature. The reference transmitted light intensity of deionized water is measured at room temperature, and therefore is not measured higher as in the case of the cleaning solution. Consequently, the transmittance calculated from the ratio therebetween includes an error due to the temperature dependent absorption coefficient of deionized water. Therefore concentration of the treating solution for use in treating substrates, based on the transmittance of the treating solution obtained by this technique is difficult to control with high precision. In particular, it is difficult to apply this technique to a substrate treating apparatus for cleaning semiconductor wafers.

A known technique to alleviate the above drawback measures the transmitted light intensity of a treating solution by introducing the treating solution continuously or intermittently from a treating bath filled with the treating solution, to a sampling pipe provided separately from the treating solution supply pipe and including a flow cell for measuring transmitted light (see Japanese Patent Laid-Open Application (Unexamined) No. Sho 62-8040, for example). According to such known technique, the treating solution sampled is cooled or allowed to cool so that the transmitted light intensity of the treating solution may be measured substantially at the same temperature as the deionized water acting as a criterion. The transmittance of the treating solution is determined with high precision, without the error due to the temperature dependence of absorption coefficient of the deionized water. As a result, concentration of the treating solution may be controlled with high precision.

However, in order to measure transmitted light intensity of the treating solution with the conventional technique referred to above, it is necessary to introduce the treating solution into the sampling pipe and cool the solution or allow it to cool to the same temperature as the deionized water acting as a criterion. Thus, the conventional technique, while providing the advantage of measuring and controlling the concentration of the treating solution with high precision, suffers a poor responsivity to variation in the concentration of the treating solution in that time is consumed in cooling the treating solution or allowing it to cool.

SUMMARY OF THE INVENTION

The present invention has been made having regard to the state of the art noted above, and the primary object of the present invention is to provide a concentration controlling method of high precision and excellent responsivity, and a substrate treating apparatus utilizing this method, which method includes making a correction to the temperature dependence of a treating solution.

The above object is fulfilled, according to a first aspect of the present invention, by a method for controlling concentration of a treating solution for use in treatment of substrates, based on a transmitted light intensity of the treating solution measured with first transmitted light intensity measuring means, and a transmitted light intensity of a solvent forming part of the treating solution measured with second transmitted light intensity measuring means. The method comprises a standard setting process including the steps of:

(a) measuring transmitted light intensities of the solvent only with the first transmitted light intensity measuring means, while varying temperature of the solvent, and storing calibration curve data showing the relationship between the temperatures and transmitted light intensities of the solvent;

(b) measuring transmitted light intensity of a standard treating solution prepared at a predetermined concentration and temperature in advance, as a standard transmitted light intensity, with the first transmitted light intensity measuring means;

(c) measuring transmitted light intensity of the solvent with the second transmitted light intensity measuring means, as a referenced transmitted light intensity;

(d) based on the temperature of the standard treating solution and the stored calibration curve data, computing an estimated transmitted light intensity corresponding to a transmitted light intensity of the solvent to be measured with the second transmitted light intensity measuring means when the solvent is adjusted to the same temperature as the standard treating solution, and computing a correction factor based on a ratio between the reference transmitted light intensity and the estimated transmitted light intensity; and (e) computing transmittance of the standard treating solution at the predetermined temperature, as a standard transmittance, from the standard transmitted light intensity, the reference transmitted light intensity and the correction factor; and executing a feedback control process including the steps of:

(f) using the first transmitted light intensity measuring means to measure the transmitted light intensity of the treating solution for actual use in treatment of substrates, as a sample transmitted light intensity;

(g) computing transmittance of the treating solution, as a sample transmittance, from the sample transmitted light intensity, the reference transmitted light intensity and the correction factor; and (h) controlling concentration of the treating solution for actual use in treatment of substrates, based on the standard transmittance and the sample transmittance;

the feedback control process being repeated to bring the standard transmittance and the sample transmittance into agreement.

In the above method, a transmittance is computed based on a ratio between the transmitted light intensity of a treating solution and the transmitted light intensity of a solvent included therein. Concentration of the treating solution is controlled based on the transmittance so computed.

As is well known, this transmittance is expressed by the following equation according to Lambert-Beer's law:

$$T = I/I_O = exp(-\alpha \cdot d \cdot c - \alpha_v \cdot d \cdot c_v) \quad (1)$$

where $I_O$ is an light intensity incident on a medium, I is a light intensity transmitted through said medium, and $\alpha$ is an absorption coefficient inherent to the medium according to Lambert-Beer's law. Here, absorption coefficient $\alpha$ represents an absorption coefficient of the treating solution, and $\alpha_v$ an absorption coefficient of the solvent. Similarly, concentration "c" is a concentration of the treating solution, and concentration "$c_v$" a concentration of the solvent. Letter "d" represents an optical path formed in a flow passage of a transmitted light measuring flow cell, which corresponds to a length of passage (optical path length) of light through a liquid.

The transmittance T is determined, as shown in equation (1) above, based on a ratio between a transmitted light intensity I and an incident light intensity $I_O$ measured substantially at the same time. However, to determine the transmittance T, the intensity of light (incident light intensity $I_O$) of a light source must be measured by utilizing complicated transmitted light intensity measuring optical system. Generally, therefore, a transmitted light intensity of the solvent (reference transmitted light intensity) is measured to serve as a criterion or standard, instead of measuring incident light intensity, and a ratio of the transmitted light intensity of the treating solution (sample transmitted light intensity) to the reference transmitted light intensity is regarded as the transmittance. Thus, in addition to the flow cell (hereinafter called the sample flow cell) for measuring the transmitted light intensity of the treating solution, a transmitted light measuring flow cell (hereinafter called the reference flow cell) having the same optical path length "d" is used, and the latter is filled with the solvent maintained at a constant temperature. A transmittance is computed based on the transmitted light intensity acquired from this reference flow cell. The treating solution is often heated for use, and therefore the transmitted light intensity thereof is widely variable due to the temperature dependence of the absorption coefficient of the treating solution. Although the sample transmitted light intensity of the treating solution varies, the solvent in the reference cell is maintained substantially at a constant temperature without being heated, so that the reference transmitted light intensity is substantially invariable. Consequently, the transmittance computed based on a ratio therebetween includes an error due to the temperature dependence of the absorption coefficient of the treating solution.

The method according to the present invention determines transmittance of the treating solution free of an error by correcting the temperature dependence of the absorption coefficient thereof in the following sequence, and carries out concentration control based on this transmittance.

First, transmitted light intensities of only the solvent are measured with the first transmitted light intensity measuring means, while varying solvent temperature. Calibration curve data showing relationships between temperatures t and transmitted light intensities I of the solvent are stored (step (a)). Generally, this calibration curve data show that the transmitted light intensity increases with temperature.

Next, a treating solution is prepared at a predetermined concentration "c" and temperature "tm" in advance, to act as a "standard treating solution". The transmitted light intensity of this standard treating solution (standard transmitted light intensity $I_R$) is measured with the first transmitted light intensity measuring means (step (b)). The standard transmitted light intensity $I_R$ is expressed as follows:

$$I_R = I_O exp(-\alpha \cdot d \cdot c - \alpha_v(te) \cdot n \cdot d \cdot c_v) \quad (2)$$

where $\alpha_v(te)$ represents an absorption coefficient of the standard treating solution at the constant temperature tm.

A transmitted light intensity of the solvent (reference transmitted light intensity $I_V$) is measured with the second transmitted light intensity measuring means for use as a criterion (step (c)). This solvent is maintained at a predetermined temperature $t_v$. The reference transmitted light intensity $I_V$ is expressed as follows:

$$I_V = I_O exp(-\alpha_v(t_v) \cdot d \cdot c_v) \quad (3)$$

where $\alpha_v(t_v)$ represents an absorption coefficient of the solvent at the temperature $t_v$.

Next, a computation is made to obtain an estimate of a transmitted light intensity of the solvent to be measured with the second transmitted light intensity measuring means (estimated transmitted light intensity $I_F$) when the solvent is maintained at the same temperature te as the standard treating solution. This computation is made, using the calibration curve data stored at step (a) above. The estimated transmitted light intensity $I_F$ is expressed by the following equation:

$$I_F = I_O exp(-\alpha_v(te) \cdot d \cdot c_v) \quad (4)$$

A correction factor K is determined as a ratio between reference transmitted light intensity $I_V$ and the estimated transmitted light intensity $I_F$ that is based on the calibration curve data (step (d)).

$$K = I_V/I_f \qquad (5)$$

Transmittance of the standard treating solution at the predetermined temperature (standard transmittance $T_R$) is computed based on standard transmitted light intensity $I_R$, reference transmitted light intensity $I_V$ and correction factor K, as follows (step (e)):

$$\begin{aligned} T_R &= K \cdot I_V/I_F \qquad (6) \\ &= (I_V/I_F) \cdot (I_R/I_V) \\ &= I_R/I_F \end{aligned}$$

If equations (2) and (4) are substituted for the terms of equation (6), $$\begin{aligned} T_R &= I_0 \exp(-\alpha \cdot d \cdot c - \alpha_V(te) \cdot d \cdot c_V)/ \qquad (7) \\ &\quad I_0 \exp(-\alpha_V(te) \cdot d \cdot c_V) \\ &= \exp(-\alpha \cdot d \cdot c) \end{aligned}$$

Thus, it is seen that temperature dependence of the absorption coefficient of the solvent does not affect standard transmittance $T_R$. Standard transmittance $T_R$ is determined through the above process in advance.

Next, transmitted light intensity of a "treating solution" adjusted to the same temperature and intended to be adjusted to the same concentration as the standard treating solution is measured (sample transmitted light intensity $I_S$) with the first transmitted light intensity measuring means (step (f)). This sample transmitted light intensity $I_S$ is expressed by the following equation:

$$I_S = I_0 \exp(-\alpha \cdot d \cdot c - \alpha_V(te) \cdot d \cdot c_V) \qquad (8)$$

Then, a transmittance of the "treating solution" (sample transmittance $T_S$) is computed based on sample transmitted light intensity $I_S$, reference transmitted light intensity $I_V$ and correction factor K determined in the standard setting process (step (g)).

$$\begin{aligned} T_S &= K \cdot I_S/I_V \qquad (9) \\ &= (I_V/I_F) \cdot (I_S/I_V) \\ &= I_S/I_F \end{aligned}$$

Since sample transmitted light intensity $I_S$ and estimated transmitted light intensity $I_F$ are derived from the solvent at the same temperature "te", temperature dependence of the absorption coefficient of the solvent does not affect this sample transmittance $T_S$.

Next, the concentration of the treating solution for actual use in treatment of substrates is controlled based on standard transmittance $T_R$ and sample transmittance $T_S$ (step (h)). Both of the transmittances $T_R$ and $T_S$ are values relating to concentration "c". Thus, for example, the chemical, a gas corresponding to the chemical, or deionized water is added to the treating solution according to a difference between the two transmittances $T_R$ and $T_S$. Concentration "c" is attained by repeating the feedback control process including steps (f) through (h) above.

Concentration "c" may be derived from equations (7) and (8) in relation to sample transmittance $T_S$ and standard transmittance $T_R$, respectively, as follows:

concentration "c" of standard solution $= -(1/\alpha \cdot d) - \ln T_S$
concentration "c" of treating solution $= -(1/\alpha \cdot d) - \ln T_R$ Assuming that concentration "c" of the treating solution is "c'", the difference $\Delta c$ between the concentrations c and c' is expressed as follows:

$$\Delta c = c' - c = -(1/\alpha \cdot d) \cdot \ln(T_S/T_R)$$

It is seen, therefore, that concentration "c'" of the treating solution and concentration "c" of the standard treating solution may be brought into agreement by controlling sample transmittance $T_S$ so that its value is the same as that of standard transmittance $T_R$. The concentration control may be effected with high precision since the influence of the temperature dependence of the solvent is eliminated from sample transmittance $T_S$ and standard transmittance $T_R$ by correction factor K. Further, the concentration may be controlled with excellent responsivity since the treating solution need not be cooled to the temperature of the solvent while measuring the reference transmitted light intensity. Moreover, the concentration control is effected based on the difference between the two transmittances relating to concentrations, without determining the concentrations. There is no need for computation of the concentrations, thereby reducing the work required to make the computation.

In a second aspect of the invention, there is provided a concentration controlling method for controlling concentration of a treating solution for use in treatment of substrates, based on transmitted light intensity of the treating solution and transmitted light intensity of a solvent included in the treating solution measured with a common transmitted light intensity measuring means. This method comprises a standard setting process including steps of:

(a) measuring transmitted light intensities of only the solvent with the transmitted light intensity measuring means, while varying temperature of the solvent, and storing calibration curve data showing the relationship between the temperatures and transmitted light intensities of the solvent;

(b) measuring transmitted light intensity of a standard treating solution prepared at a predetermined concentration and temperature in advance, as a standard transmitted light intensity, with the transmitted light intensity measuring means;

(c) measuring transmitted light intensity of the solvent adjusted at a constant temperature, with the transmitted light intensity measuring means, as a reference transmitted light intensity;

(d) based on the temperature of the standard treating solution and the calibration curve data stored, computing an estimated transmitted light intensity corresponding to a transmitted light intensity of the solvent to be measured with the transmitted light intensity measuring means when the solvent is adjusted to the same temperature as the standard treating solution, and computing a correction factor based on a ratio between the reference transmitted light intensity and the estimated transmitted light intensity; and (e) computing transmittance of the standard treating solution at the predetermined temperature, as a standard transmittance, based on the standard transmitted light intensity, the reference transmitted light intensity and the correction factor; and executing a feedback control process including the steps of:

(f) measuring the transmitted light intensity of the treating solution for actual use in treatment of substrates, with the transmitted light intensity measuring means, as sample transmitted light intensity;

(g) computing a transmittance of the treating solution, as a sample transmittance, based on the sample transmitted light intensity, the reference transmitted light intensity and the correction factor; and (h) controlling the concentration of the treating solution for actual use in treatment of substrates, based on the standard transmittance and the sample transmittance;

the feedback control process being repeated to bring the standard transmittance and the sample transmittance into agreement.

This method has the same functions as the method in the first aspect of the invention excepting that the transmitted light intensities are measured with the common transmitted light intensity measuring means.

Preferably, in the first and second aspects of this invention, step (c) is executed again before step (f) to measure a new reference transmitted light intensity, and step (g) is executed after deriving the correction factor based on the ratio between the new reference transmitted light intensity and the estimated transmitted light intensity.

Then, a correction factor may be determined accurately even if variations should occur, with passage of time, in the luminous intensity of a light source included in the transmitted light intensity measuring means. This assures an accurate computation of sample transmittance.

More particularly, as noted above, sample transmittance $T_S$ is computed based on sample transmitted light intensity $I_S$, reference transmitted light intensity $I_V$ measured in the standard setting process, and correction factor K. This is based on the condition that when sample transmitted light intensity $I_S$ of the treating solution is measured, reference transmitted light intensity $I_V$ is equal to reference transmitted light intensity $I_V$ measured at the standard setting process. However, it is possible that reference transmitted light intensity $I_V$ may vary with variations in the luminous intensity of the light source or the like. With this deviating reference transmitted light intensity $I_V$ (and correction factor K, computation of which is based thereon), sample transmittance $T_S$ cannot be derived accurately by using equation (9). Under the circumstances, reference transmitted light intensity $I_V$ is measured again before this sample transmittance $T_S$ is computed. That is, a correct correction factor K may be determined and a correct sample transmittance $T_S$ computed by reducing the interval of measurement between sample transmitted light intensity $I_S$ and reference transmitted light intensity $I_V$ in the feedback control process to be much shorter than the interval between variations in luminous intensity of the light source.

Preferably, in the first and second aspects of the invention, step (a) is executed to measure source-related light intensities, relating to intensities of light emitted by the light source, at varied temperatures as well as the transmitted light intensities at the varied temperatures, and to store ratios between the transmitted light intensities and the source-related light intensities (i.e. transmitted light intensity ratios) as the calibration curve data, steps (b), (c) and (f) being executed to measure the source-related light intensities as well as the transmitted light intensities to determine ratios therebetween, and to carry out computations based on such ratios.

The source-related light intensity is, for example, the light intensity of the light source measured directly or measured through a light reducing means such as a filter. Thus, the transmitted light intensity ratios are substantially invariable even with variations in the luminous intensity of the light source. The transmitted light intensity ratios unaffected by variations in the luminous intensity of the light source are stored as calibration curve data. The source-related light intensity will be explained with taking incident light intensity $I_O$ used in equation (1) for example.

Relationships between transmitted light intensity ratios (transmitted light intensities I/incident light intensities $I_O$) and temperatures T are stored as the calibration curve data. Then, at steps (b), (c) and (f), the source-related transmitted light intensities (incident light intensities $I_O$) as well as the transmitted light intensities are measured to determine ratios therebetween. At the above steps, computations are carried out based on these ratios.

That is, at step (b), the transmitted light intensity (standard transmitted light intensity $I_R$) of the standard treating solution prepared at the predetermined concentration and temperature in advance, and incident light intensity $I_O$, are measured to determine a ratio therebetween (standard transmitted light intensity $I_R$/incident light intensity $I_O$) as standard transmitted light intensity ratio $R_R$. At step (c), the transmitted light intensity (reference transmitted light intensity $I_V$) of the solvent, and incident light intensity $I_O$, are measured to determine a ratio therebetween (reference transmitted light intensity $I_V$/incident light intensity $I_O$) as reference transmitted light intensity ratio $R_V$. At step (f), the transmitted light intensity (sample transmitted light intensity $I_S$) of the treating solution for actual use in treatment of substrate, and incident light intensity $I_O$, are measured to determine a ratio therebetween (sample transmitted light intensity $I_S$/incident light intensity $I_O$) as sample transmitted light intensity ratio $R_S$.

At step (d), estimated transmitted light intensity $R_F$ (estimated light intensity $I_F$/incident light intensity $I_O$) is determined based on the temperature of the standard treating solution and the calibration curve data. This estimated transmitted light intensity $R_F$ corresponds to the transmitted light intensity ratio acquired when the temperature of the solvent is at the same temperature as the standard treating solution. Then, correction factor K is computed based on a ratio between reference transmitted light intensity ratio $R_V$ (reference transmitted light intensity $I_V$/incident light intensity $I_O$) and estimated transmitted light intensity $R_F$ (estimated light intensity $I_F$/incident light intensity $I_O$). This correction factor K corresponds to a ratio between reference transmitted light intensity $I_V$ and estimated transmitted light intensity $I_F$. That is, $(I_V/I_O)/(I_F/I_O)$, and hence correction factor $K=I_V/I_F$. This corresponds to equation (5) set out hereinbefore. Transmitted light intensities $I_V$ and $I_F$ are variable with the luminous intensity of the light source. That is, when the luminous intensity of the light source decreases, naturally these transmitted light intensities will decrease too. However, instead of using transmitted light intensities $I_V$ and $I_F$ as they are, the ratios thereof to the source-related light intensity (incident light intensity $I_O$) are used. Such ratios are not affected by variations in the luminous intensity of the light source. Thus, the respective values may be computed accurately even if variations should occur in the luminous intensity of the light source between a point in time at which the calibration curve data are acquired and a point in time at which each transmitted light intensity is measured.

At step (e), transmittance of the standard treating solution (standard transmittance $T_R$) is computed based on standard transmitted light intensity ratio $R_R$ ($=I_R/I_O$), reference transmitted light intensity ratio $R_V$ ($=I_V/I_O$) and correction factor K ($=I_V/I_F$). Standard transmittance $T_R$ is expressed by $T_R=K \cdot R_R/R_V$. Thus:

$$T_R = (I_V/I_F) \cdot (I_R/I_O)/(I_V/I_O)$$
$$= (I_V/I_F) \cdot (I_R/I_V)$$
$$= I_R/I_F$$

This corresponds to equation (6), or equation (7), set out hereinbefore. It will be seen that standard transmittance $T_R$ is free from the temperature dependence of the absorption coefficient of the solvent.

At step (f), sample transmitted light intensity $I_S$/incident light intensity $I_O$ is determined as sample transmitted light intensity ratio $R_S$. At step (g), sample transmittance $T_S$ of the treating solution is computed based on sample transmitted light intensity ratio $R_S$ ($=I_S/I_O$), reference transmitted light intensity ratio $R_V$ ($=I_V/I_O$) and correction factor K ($=I_V/I_F$). Sample transmittance $T_S$ is expressed by $T_S = K \cdot R_S/R_V$. Thus:

$$T_S = (I_V/I_F) \cdot (I_S/I_O)/(I_V/I_O)$$
$$= I_V/I_F \cdot I_S/I_V$$
$$= I_S/I_F$$

It will be seen that this corresponds to equation (9) set out hereinbefore.

In addition, standard transmittance $T_R$ and sample transmittance $T_S$ are computed accurately even if variations should occur in the intensity of the light source, since their computation is based on the ratios thereof to incident light intensity $I_O$ which is the source-related light intensity. As a result, the concentration control may be effected accurately over a long period of time, without being affected by variations in the luminous intensity of the light source.

A third aspect of the invention relates to a substrate treating apparatus utilizing the method in the first aspect of the invention.

Thus, in the third aspect of the invention, there is provided a substrate treating apparatus for treating substrates with a treating solution adjusted to a predetermined concentration and temperature, comprising:

substrate holding means for holding the substrate to be treated;

treating solution storage means for storing the treating solution for treating the substrate held by the substrate holding means;

chemical supply means for supplying a chemical or a gas thereof forming part of the treating solution to the treating solution storage means;

solvent supply means for supplying a solvent included in the treating solution to the treating solution storage means;

treating solution supply means for supplying the treating solution stored in the treating solution storage means to the substrate held by the substrate holding means;

first and second sampling means for sampling an object to be measured with having optical paths of the same length, respectively;

first transmitted light intensity measuring means for measuring, with the first sampling means, a standard transmitted light intensity of a standard treating solution prepared at the predetermined concentration and temperature in advance, and for measuring a sample transmitted light intensity of a treating solution for actual use in treatment of substrates, with the first transmitted light intensity measuring means;

second transmitted light intensity measuring means for measuring a transmitted light intensity (reference transmitted light intensity) of the solvent with the second sampling means;

calibration curve data collecting means for measuring transmitted light intensities of only the solvent with the first sampling means, while varying temperature of the solvent, and collecting calibration curve data showing relationships between the temperatures and transmitted light intensities of the solvent;

correction factor computing means for computing, based on the temperature of the standard treating solution and the calibration curve data collected, an estimated transmitted light intensity corresponding to a transmitted light intensity of the solvent measured with the second sampling means and the second transmitted light intensity measuring means when the solvent is adjusted to the same temperature as the standard treating solution, and computing a correction factor from a ratio between the reference transmitted light intensity and the estimated transmitted light intensity;

standard transmittance computing means for computing transmittance of the standard treating solution at the predetermined temperature, as a standard transmittance, based on the standard transmitted light intensity, the reference transmitted light intensity and the correction factor;

sample transmittance computing means for computing transmittance of the treating solution, as a sample transmittance, based on the sample transmitted light intensity, the reference transmitted light intensity and the correction factor; and concentration control means for controlling the concentration of the treating solution for actual use in treatment of substrates, by controlling the chemical supply means and the solvent supply means based on the standard transmittance and the sample transmittance.

This substrate treating apparatus has the following functions.

First, using the first sampling means, the calibration curve data collecting means measures transmitted light intensities of the solvent while varying temperature of the solvent, and collects calibration curve data showing the relationship between the temperatures and transmitted light intensities of the solvent.

Then, using the first sampling means, the first transmitted light intensity measuring means measures a transmitted light intensity (standard transmitted light intensity) of a standard treating solution prepared at the predetermined concentration and temperature in advance. The second transmitted light intensity measuring means also measures a transmitted light intensity (reference transmitted light intensity) of the solvent with the second sampling means.

Subsequently, based on the temperature of the standard treating solution and the calibration curve data collected, the correction factor computing means computes a transmitted light intensity (estimated transmitted light intensity) of the solvent measured when the solvent is adjusted to the same temperature as the standard treating solution, and computes a correction factor based on a ratio between the reference transmitted light intensity and the estimated transmitted light intensity. The standard transmittance computing means computes a transmittance of the standard treating solution (standard transmittance) at the predetermined temperature based on the standard transmitted light intensity, the reference transmitted light intensity and the correction factor. In this way, the temperature dependence of the standard transmittance is corrected with the correction factor, to compute the standard transmittance accurately.

Next, the first transmitted light intensity measuring means measures a transmitted light intensity (sample transmitted light intensity) of a treating solution for actual use in treatment of substrates. The sample transmittance computing means computes a transmittance of the treating solution (sample transmittance) based on the sample transmitted light intensity, the reference transmitted light intensity and the correction factor. In this way, the temperature dependence of the sample transmittance is corrected with the correction factor, thereby to compute the sample transmittance accurately.

Then, the concentration control means adjusts the concentration of the treating solution stored in the treating solution storage means, by controlling the chemical supply means and solvent supply means based on the standard transmittance and the sample transmittance. The treating solution with the concentration adjusted is supplied to the substrate in the substrate holding means.

A fourth aspect of this invention relates to a substrate treating apparatus utilizing the method in the second aspect of the invention.

Thus, in the fourth aspect of the invention, there is provided a substrate treating apparatus for treating substrates with a treating solution adjusted to a predetermined concentration and temperature. Such treating apparatus includes:

substrate holding means for holding a substrate to be treated;

treating solution storage means for storing the treating solution for treating the substrate held by the substrate holding means;

chemical supply means for supplying a chemical or a gas thereof for forming part of the treating solution to the treating solution storage means;

solvent supply means for supplying a solvent included in the treating solution to the treating solution storage means;

treating solution supply means for supplying the treating solution stored in the treating solution storage means to the substrate held by the substrate holding means;

sampling means, having a light transmitting portion through which light incident thereon is transmitted, for separately sampling the treating solution and the solvent;

light emitting means for emitting light toward the light transmitting portion of the sampling means;

light receiving means for receiving light transmitted through the light transmitting portion of the sampling means to measure intensity of light transmitted therethrough;

light detecting means for detecting intensity of light emitted by the light emitting means;

transmitted light intensity ratio determining means, that utilizes the sampling means, the light emitting means, the light receiving means and the light detecting means, for determining a standard transmitted light intensity ratio between a transmitted light intensity of a standard treating solution prepared at the predetermined concentration and temperature, and intensity of light detected by the light detecting means, for determining a reference transmitted light intensity ratio between a reference transmitted light intensity representing an intensity of light transmitted through only the solvent and intensity of light detected by the light detecting means, and for determining a sample transmitted light intensity ratio between a sample transmitted light intensity representing an intensity of light transmitted through a treating solution for actual use in substrate treatment and intensity of light detected by the light detecting means;

calibration curve data collecting means for measuring transmitted light intensities of only the solvent by using the light emitting means, the light receiving means, and the sampling means, while varying temperature of the solvent, and collecting calibration curve data showing a relationship between the temperatures and transmitted light intensities of the solvent;

correction factor computing means for computing, based on the temperature of the standard treating solution and the calibration curve data collected, a ratio between an estimated transmitted light intensity ratio corresponding to a transmitted light intensity of the solvent measured with the sampling means when the solvent is adjusted to the same temperature as the standard treating solution, and the intensity of light emitted from the light emitting means, as an estimated transmitted light intensity ratio, and computing a correction factor based on a ratio between the reference transmitted light intensity ratio and the estimated transmitted light intensity ratio;

standard transmittance computing means for computing transmittance of the standard treating solution at the predetermined temperature, as a standard transmittance, based on the standard transmitted light intensity ratio, the reference transmitted light intensity ratio and the correction factor;

sample transmittance computing means for computing transmittance of the treating solution, as a sample transmittance, based on the sample transmitted light intensity ratio, the reference transmitted light intensity ratio and the correction factor; and concentration control means for controlling the concentration of the treating solution for actual use in treatment of a substrate, by controlling the chemical supply means and the solvent supply means based on the standard transmittance and the sample transmittance.

The substrate treating apparatus in the fourth aspect of this invention differs from the apparatus in the third aspect of this invention in that the common sampling means is used for sampling the treating solution and solvent, and in that the source-related light intensity is measured.

The calibration curve data collecting means measures transmitted light intensities of the solvent with the sampling means, while varying temperature of the solvent, and collects calibration curve data showing a relationship between the temperatures and transmitted light intensities of the solvent.

Then, with the sampling means, the transmitted light intensity ratio measuring means measures transmitted light intensity (standard transmitted light intensity) of a standard treating solution prepared at the predetermined concentration and temperature in advance, and the intensity of light emitted by the light emitting means (source-related light intensity). Then, the transmitted light intensity ratio determining means determines the ratio between the standard transmitted light intensity and source-related light intensity. Further, the transmitted light intensity ratio determining means measures transmitted light intensity (reference transmitted light intensity) of only the solvent passed through the sampling means, and determines the ratio (reference transmitted light intensity ratio) between the reference transmitted light intensity and the source-related light intensity.

Subsequently, based on the temperature of the standard treating solution and the calibration curve data collected, the correction factor computing means computes a transmitted light intensity (estimated transmitted light intensity) of the solvent measured when the solvent is adjusted to the same temperature as the standard treating solution, and computes a ratio (estimated transmitted light intensity ratio) between the estimated transmitted light intensity and source-related light intensity. Then, the correction factor computing means computes a correction factor based on the ratio between the reference transmitted light intensity ratio and estimated transmitted light intensity ratio. This source-related light intensity is involved in both the reference transmitted light intensity ratio and estimated transmitted light intensity ratio.

Therefore, both of these ratios are variable with variations occurring in the luminous intensity of the light emitting means. Thus, the influences of variations occurring in the luminous intensity of the light emitting means are not reflected in the ratio between the reference transmitted light intensity ratio and estimated transmitted light intensity ratio (reference transmitted light intensity ratio/estimated transmitted light intensity ratio), whereby the correction factor is computed accurately.

Then, the standard transmittance computing means computes transmittance of the standard treating solution (standard transmittance) at the predetermined temperature from the standard transmitted light intensity ratio, the reference transmitted light intensity ratio and the correction factor. In this way, the temperature dependence of the standard transmittance is corrected with the correction factor, whereby the standard transmittance is computed accurately.

Next, the transmitted light intensity ratio determining means measures a transmitted light intensity (sample transmitted light intensity) of a treating solution for actual use in treatment of substrates, and determines the ratio (sample transmitted light intensity ratio) between the sample transmitted light intensity and source-related light intensity.

The sample transmittance computing means computes transmittance of the treating solution (sample transmittance) based on the sample transmitted light intensity ratio, the reference transmitted light intensity ratio and the correction factor. In this way, the temperature dependence of the sample transmittance is corrected with the correction factor, whereby the sample transmittance is computed accurately. Furthermore, the respective ratios are invariable with variations in the luminous intensity of the light emitting means since these ratios are based on the ratios between transmitted light intensity and source-related light intensity. The sample transmittance is computed accurately without being affected by variations in the luminous intensity of the light emitting means.

Then, the concentration control means adjusts the concentration of the creating solution stored in the treating solution storage means, by controlling the chemical supply means and solvent supply means based on the standard transmittance and the sample transmittance. The treating solution with the concentration adjusted is supplied to the substrate in the substrate holding means.

Preferably, in the substrate treating apparatus in the third and fourth aspects of the invention, the concentration control means includes a feedback control means for controlling the chemical supply means and the solvent supply means based on a difference between the standard transmittance and the sample transmittance.

Preferably, in the substrate treating apparatus of the third and fourth aspects of this invention, at least the sampling means includes a transmitted light measuring flow cell having an opposed pair of light transmitting elements formed of a translucent material and spaced from each other by a predetermined distance (cell length), light entering the flow cell through one of the light transmitting elements to irradiate an object fluid flowing between the transmitting elements, intensity of light emerging through the other light transmitting element being measured, the flow cell having coatings that are corrosion-resistant with respect to the object fluid and formed on surfaces of the light transmitting elements exposed to the object fluid. By covering the light transmitting elements with the corrosion-resistant coatings, the transmitting elements are protected from corrosion by the treating solution. The material forming the transmitting elements is thereby prevented from dissolving into the treating solution.

Preferably, the coatings are formed of a fluororesin which is corrosion-resistant to varied chemicals and has excellent heat resistance as well.

Preferably, in the substrate treating apparatus according to the third aspect of the invention, the first and second transmitted light intensity measuring means includes a single common light source, a light divider for dividing light emitted from the light source for the first and second sampling means, a single optical detector for receiving divided parts of light transmitted through the first and second sampling means, and outputting signals corresponding to intensities of the divided parts of light, respectively, and an optical path switcher for alternately causing the divided parts of light to enter the optical path switcher, the signals being accepted from the optical detector synchronously with switching action of the optical path switcher, such that an output signal of the optical detector accepted when the optical detector receives light transmitted through the second sampling means is measured as the reference transmitted light intensity, and an output signal of the optical detector accepted when the optical detector receives light transmitted through the first sampling means is measured as the standard transmitted light intensity.

Similarly, it is preferred that, in the substrate treating apparatus according to the fourth aspect of this invention, the transmitted light intensity measuring means includes a single light source, an optical filter having a predetermined reduction ratio, a light divider for dividing light emitted from the light source for the sampling means and the optical filter, a single optical detector for receiving divided parts of light transmitted through the sampling means and the optical filter, and outputting signals corresponding to intensities of the divided parts of light, respectively, and an optical path switcher for alternately causing the divided parts of light to enter the optical path switcher, the signals being accepted from the optical detector synchronously with switching action of the optical path switcher, such that an output signal of the optical detector accepted when the optical detector receives light transmitted through the sampling means is measured as one of the standard transmitted light intensity, the reference transmitted light intensity and the sample transmitted light intensity, and an output signal of the optical detector accepted when the optical detector receives light transmitted through the optical filter is measured as an intensity of light (source-related light intensity) emitted from the light emitter.

With the above constructions, the light emitted from the single light source is transmitted in two divided parts through the first and second sampling means in the apparatus according to the third aspect of this invention (through the sampling means and optical filter in the fourth aspect of this invention). The two parts of light are allowed by the optical path switcher to enter the single optical detector alternately. Variations in the luminous intensity of the light source and in the sensitivity of the optical detector that occur as time passes influence the reference transmitted light intensity, sample transmitted light intensity and standard transmitted light intensity (and the source-related light intensity in the apparatus according to the fourth aspect of this invention). Consequently, by determining ratios between these light intensities, the influences of variations occurring in the luminous intensity of the light source cancel each other, thereby permitting accurate control of the concentration of the treating solution to be obtained.

Preferably, the optical path switcher includes a light selecting shutter in the form of a plate having a light transmitting portion and a light shielding portion formed in a predetermined ratio, and a drive means for driving the light shielding shutter for alternately allowing the light transmitted through the second sampling means and the light transmitted through the first sampling means to irradiate the optical detector in the apparatus according to the third aspect of this invention (through the sampling means and optical filter in the apparatus according to the fourth aspect of this invention). With this construction, the divided parts of light transmitted through the first and second sampling means in the apparatus according to the third aspect of this invention (through the sampling means and optical filter according to the fourth aspect of this invention) are allowed to irradiate the optical detector alternately within a short time compared with time during which variations occur in the luminous intensity of the light source and in the sensitivity of the optical detector. This further diminishes the influences of variations in the luminous intensity of the light source and in the sensitivity of the optical detector.

Preferably, in the apparatus according to the third aspect of this invention, the first and second transmitted light intensity measuring means are operable to repeat measurement of the standard transmitted light intensity and the sample transmitted light intensity, and measurement of the reference transmitted light intensity, and to compute moving averages of ratios between transmitted light intensities and reference transmitted light intensities adjacent each other in time, i.e. a ratio between an (i)th ("i" being a natural number) transmitted light intensity and an (i)th reference transmitted light intensity, a ratio between an (i+1)th transmitted light intensity and the (i)th reference transmitted light intensity, and a ratio between the (i+1)th transmitted light intensity and the (i+1)th reference transmitted light intensity.

Similarly, it is preferred that, in the substrate treating apparatus according to the fourth aspect of this invention, the transmitted light intensity measuring means is operable to repeat measurement of the standard transmitted light intensity, the reference transmitted light intensity and the sample transmitted light intensity, and measurement of the source-related light intensity, and to compute moving averages of ratios between transmitted light intensities and source-related light intensities adjacent each other in time, i.e. a ratio between an (i)th ("i" being a natural number) transmitted light intensity and an (i)th source-related light intensity, a ratio between an (i+1)th transmitted light intensity and the (i)th source-related light intensity, and a ratio between the (i+1)th transmitted light intensity and the (i+1)th source-related light intensity, the moving averages being used as a standard transmitted light intensity ratio, a reference transmitted light intensity ratio and a sample transmitted light intensity ratio, respectively.

In the third aspect of this invention, it would be ideal to measure the sample transmitted light intensity (or the standard transmitted light intensity) and the reference transmitted light intensity simultaneously. Similarly, in the fourth aspect of this invention, it would be ideal to measure the sample transmitted light intensity (or the standard or reference transmitted light intensity) and the source-related light intensity simultaneously. In practice, however, in the apparatus according to the third aspect of this invention, for example, considerable time is required for optical path switching if the reference transmitted light intensity and sample transmitted light intensity are detected with the single optical detector. In the case of the apparatus according to the fourth aspect of this invention, considerable time is required for switching between the treating solution and the solvent since only one sampling means is used.

In the apparatus according to the third aspect of this invention, therefore, the reference transmitted light intensity and sample transmitted light intensity are measured one before the other. Then, the output signal of the optical detector is variable with time. This causes the sample transmitted light intensity, for example, to increase with time despite a constant temperature of the fluid. The reference transmitted light intensity also increases with time. Assuming that the sample transmitted light intensity and reference transmitted light intensity are equal (thus, the ratio therebetween is "1" in an ideal, simultaneous measurement of these transmitted light intensities) and assuming that the sample transmitted light intensity is measured first, a relationship in strength may be expressed as follows:

$$I_{S1} < I_{R1} < I_{S2} < I_{R2} < I_{S3} < I_{R3} < I_{S4} < I_{R4} \cdots$$

where $I_{Sn}$ ("n" indicates a place in order of measurement) is the sample transmitted light intensity, and $I_{Rn}$ is the reference transmitted light intensity.

The ratio (transmittance $T_{11}=I_{S1}/I_{R1}$) between the first sample transmitted light intensity $I_{S1}$ and first reference transmitted light intensity $I_{R1}$, the ratio (transmittance $T_{21}=I_{S2}/I_{R1}$) between the second sample transmitted light intensity $I_{S2}$ and first reference transmitted light intensity $I_{R1}$, and subsequent transmittances are in the following relationship:

$$T_{11} < T_{21} > T_{22} < T_{32} > T_{33} < \cdots$$

Compared with the ideal, simultaneous measurement, $$T_{11} < 1,\ 1 < T_{21},\ 1 > T_{22},\ 1 < T_{32},\ 1 > T_{33} \cdots$$

Thus, the transmittances are in the relationship to repeat "smaller" and "greater" compared with the ideal measurement. By computing moving averages of the ratios between sample transmitted light intensities and reference transmitted light intensities adjacent each other in time in the above relationship, it is possible to obtain values close to ideal values resulting from a simultaneous measurement of sample transmitted light intensity and reference transmitted light intensity. Thus, the ratios between sample transmitted light intensity and reference transmitted light intensity may be obtained with high precision by suppressing the influences of variations in the optical detector. This applies to the apparatus according to the fourth aspect of this invention also.

Assume that transmittances are obtained in a different way. That is, the ratio (transmittance $T_{11}=I_{S1}/I_{R1}$) between the first sample transmitted light intensity $I_{S1}$ and first reference transmitted light intensity $I_{R1}$, the ratio (transmittance $T_{22}=I_{S2}/I_{R2}$) between the second sample transmitted light intensity $I_{S2}$ and second reference transmitted light intensity $I_{R2}$, and subsequent transmittances are in the following relationship:

$$T_{11} < T_{22} < T_{33} < \cdots$$

Compared with the ideal, simultaneous measurement, $$T_{11} < 1,\ T_{22} < 1,\ T_{33} < 1 \cdots$$

Thus, the transmittances are in the relationship to repeat "smaller" only, compared with the ideal measurement.

Obviously, it is impossible to obtain values close to ideal values by computing moving averages of such ratios.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DETAILED DESCRIPTION OF THE PREFERRED EMBODIMENTS

Preferred embodiments of the present invention will be described in detail hereinafter with reference to the drawings.

A. Apparatus in the First Embodiment (Substrate Treating Apparatus Utilizing the Method in the First Aspect of the Invention)

Figure 1:
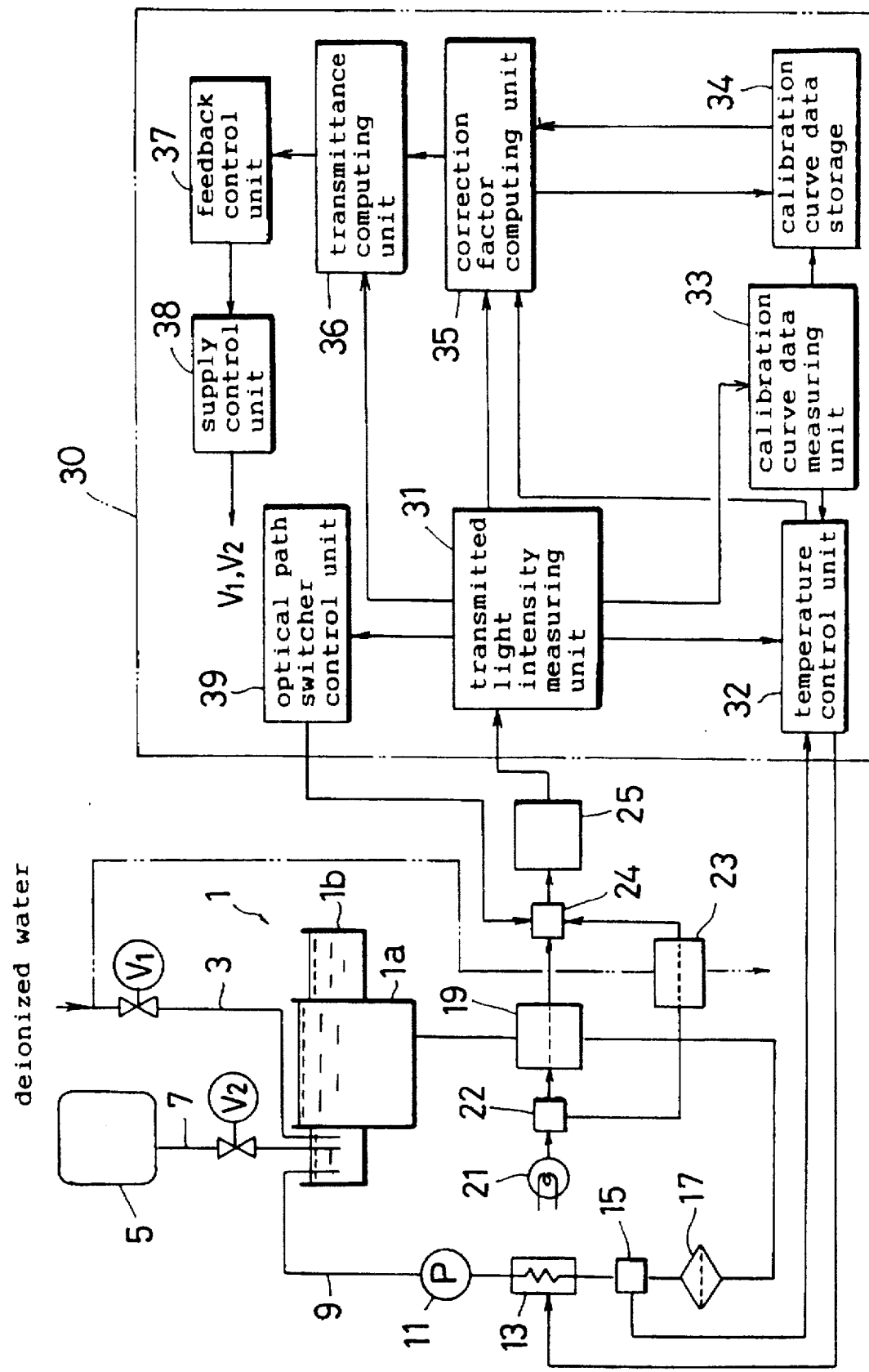
FIG. 1 is a schematic of a substrate treating apparatus constructed according to a first embodiment of the present invention.

Numeral 1 in FIG. 1 denotes an overflow type treating bath that includes a main treating vessel 1a for immersing therein a wafer carrier holding a plurality of semiconductor wafers, and an overflow vessel 1b surrounding the main treating vessel 1a for storing a treating solution overflowing the main treating vessel 1a. The overflow vessel 1b receives deionized water under pressure through deionized water supply piping 3. The deionized water supply is adjustable by a flow control valve V1. The overflow vessel 1b also receives a chemical from a chemical tank 5 through chemical supply pipe 7. The chemical supply is adjustable by a flow control valve V2. The chemical and deionized water are mixed in the overflow vessel 1b to form the treating solution. The deionized water supply pipe 3 corresponds to the solvent supplying means of the present invention. The chemical tank 5 and chemical supply pipe 7 correspond to the chemical supplying means.

One end of treating solution supply pipe 9 is connected to the overflow vessel 1b to form a circulating path of the treating solution. This pipe 9 includes a pump 11 for circulating the treating solution, a heater 13 for heating the solution in circulation to a predetermined temperature, a temperature sensor 15 for measuring temperatures of the solution, a filter 17 for removing particles and the like from the solution, and a sampling flow cell 19 having an optical path of a predetermined optical path length "d". The other end of pipe 9 is connected to a bottom of the main treating vessel 1a at the bottom thereof.

Light from a light source 21 such as a halogen lamp is divided by a light divider 22 to travel in two directions. One divided part of the light irradiates the sampling flow cell 19. The other part irradiates a reference cell 23 having the predetermined optical path length "d" filled with deionized water. The deionized water for filling the reference cell 23 may be caused to flow, when necessary, as shown in a two-dot-and-dash line in FIG. 1, as long as the deionized water is maintained at a fixed temperature, e.g. room temperature. The two parts of light transmitted through the sample flow cell 19 and reference cell 23 travel to an optical path switcher 24. This switcher 24 selects one part of light to be incident on an optical detector 25. The light source 21, light divider 22, optical path switcher 24 and optical detector 25 correspond to the transmitted light intensity detecting means of the present invention. Separate light sources of the same luminous intensity and separate optical detectors of the same sensitivity may be provided for the sample flow cell 19 and reference cell 23, respectively. In this case, the light divider 22 and optical path switcher 24 are omitted from the apparatus.

A signal relating to a transmitted light intensity detected by the optical detector 25 is applied to a concentration controller 30. Broadly, concentration controller 30 includes a transmitted light intensity measuring unit 31, a temperature control unit 32, a calibration curve data measuring unit 33, a calibration curve data storage 34, a correction factor computing unit 35, a transmittance computing unit 36, a feedback control unit 37, a supply control unit 38 and an optical path switcher control unit 39. The transmitted light intensity measuring unit 31 corresponds to the transmitted light intensity measuring means of the present invention. The temperature control unit 32, heater 13 and temperature sensor 15 corresponded to the temperature control means. The calibration curve data measuring unit 33 corresponds to the calibration curve data measuring means. The calibration curve data storage 34 corresponds to the calibration curve data storage means. The correction factor computing unit 35 corresponds to the correction factor computing means. The transmittance computing unit 36 corresponds to the transmittance computing means. The feedback control unit 37 corresponds to the feedback control means. The supply control unit 38 and flow control valves $V_1$ and $V_2$ correspond to the supply control means of the present invention.

The transmitted light intensity measuring unit 31 causes the optical path switcher control unit 39 to couple the optical path switcher 24 to the sample flow cell 19, while circulating through the treating solution supply pipe 9 a "standard treating solution" adjusted to a predetermined concentration by a standard treating solution adjusting means (not shown), and measures through the sample flow cell 19 the transmitted light intensity (standard transmitted light intensity $I_R$) of this solution adjusted to a predetermined temperature by using the temperature control unit 32, heater 13 and temperature sensor 15. Substantially at the same time, the transmitted light intensity measuring unit 31 causes the switcher control unit 39 to couple the optical path switcher 24 to the reference cell 23, and measures the transmitted light intensity (reference transmitted light intensity $I_V$). Each transmitted light intensity measured is passed on to the correction factor computing unit 35 and transmittance computing unit 36.

While circulating a treating solution adjusted to the same temperature and intended to be adjusted to the same concentration as that of the standard treating solution, the transmitted light intensity measuring unit 31 causes the switcher control unit 39 to couple the optical path switcher 24 to the sample flow cell 19, and measures its transmitted light intensity (sample transmitted light intensity $I_S$). Substantially at the same time, the transmitted light intensity measuring unit 31 causes the switcher control unit 39 to couple the optical path switcher 24 to the reference cell 23, and measures the transmitted light intensity (reference transmitted light intensity $I_V$). Each transmitted light intensity measured is passed on to the transmittance computing unit 36.

The calibration curve data measuring unit 33, in the condition in which only the solvent (i.e. deionized water in this embodiment) contained in the treating solution to flowing through the sample flow cell 19, acquires transmitted light intensities from the transmitted light intensity measuring unit 31 with varying the temperature of the deionized water through the temperature control unit 32. Calibration curve data showing the relationship between the temperature and transmitted light intensity of the solvent is stored in the calibration curve data storage 34.

The correction factor computing unit 35 computes estimated transmitted light intensity $I_F$ based on the temperature of the standard treating solution or of the treating solution for use in treatment of wafers, and the calibration curve data stored in the calibration curve data storage 34. The estimated transmitted light intensity $I_F$ corresponds to the reference transmitted light intensity where the solvent contained in the treating solution is at the same temperature as the standard treating solution or the treating solution for use in treatment of wafers. The correction factor computing unit 35 then computes correction factor K based on the ratio between reference transmitted light intensity $I_V$ and the estimated transmitted light intensity $I_F$.

The transmittance computing unit 36 computes the transmittance of the standard treating solution (standard transmittance $T_R$) based on the standard transmitted light intensity $I_R$, the reference transmitted light intensity $I_V$, and the correction factor K computed by the correction factor computing unit 35, and the transmittance of the treating solution (sample transmittance $T_S$) based on the sample transmitted light intensity $I_S$, the reference transmitted light intensity $I_V$ and correction factor K.

The feedback control unit 37 receives the standard transmittance $T_R$ and the sample transmittance $T_S$ from the transmittance computing unit 36, and outputs to the supply control unit 38 a control signal reflecting a difference between the standard transmittance $T_R$ and the sample transmittance $T_S$. In response to the control signal, the supply control unit 38 effects an appropriate adjustment of the flow control valve V1 provided on the deionized water supply pipe 3 or the flow control valve V2 provided on the chemical supply pipe 7 to adjust the concentration of the treating solution for use in treatment of wafers.

Figure 2:
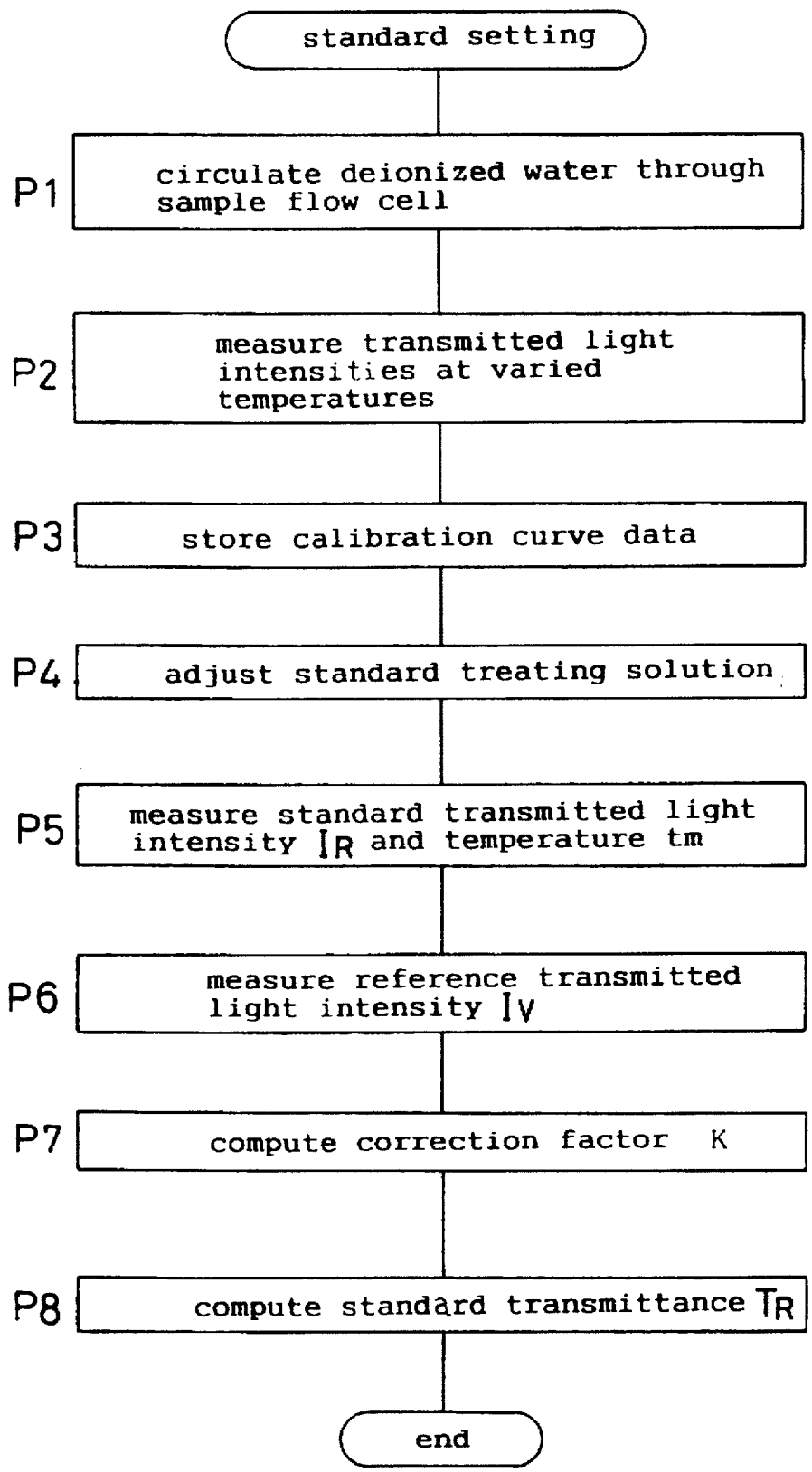
FIG. 2 is a flowchart of a standard setting process for the first embodiment.

A first to be executed standard setting sequence will now be described with reference to the flowchart shown in FIG. 2. This sequence corresponds to the standard setting process of the present invention.

Figure 3:
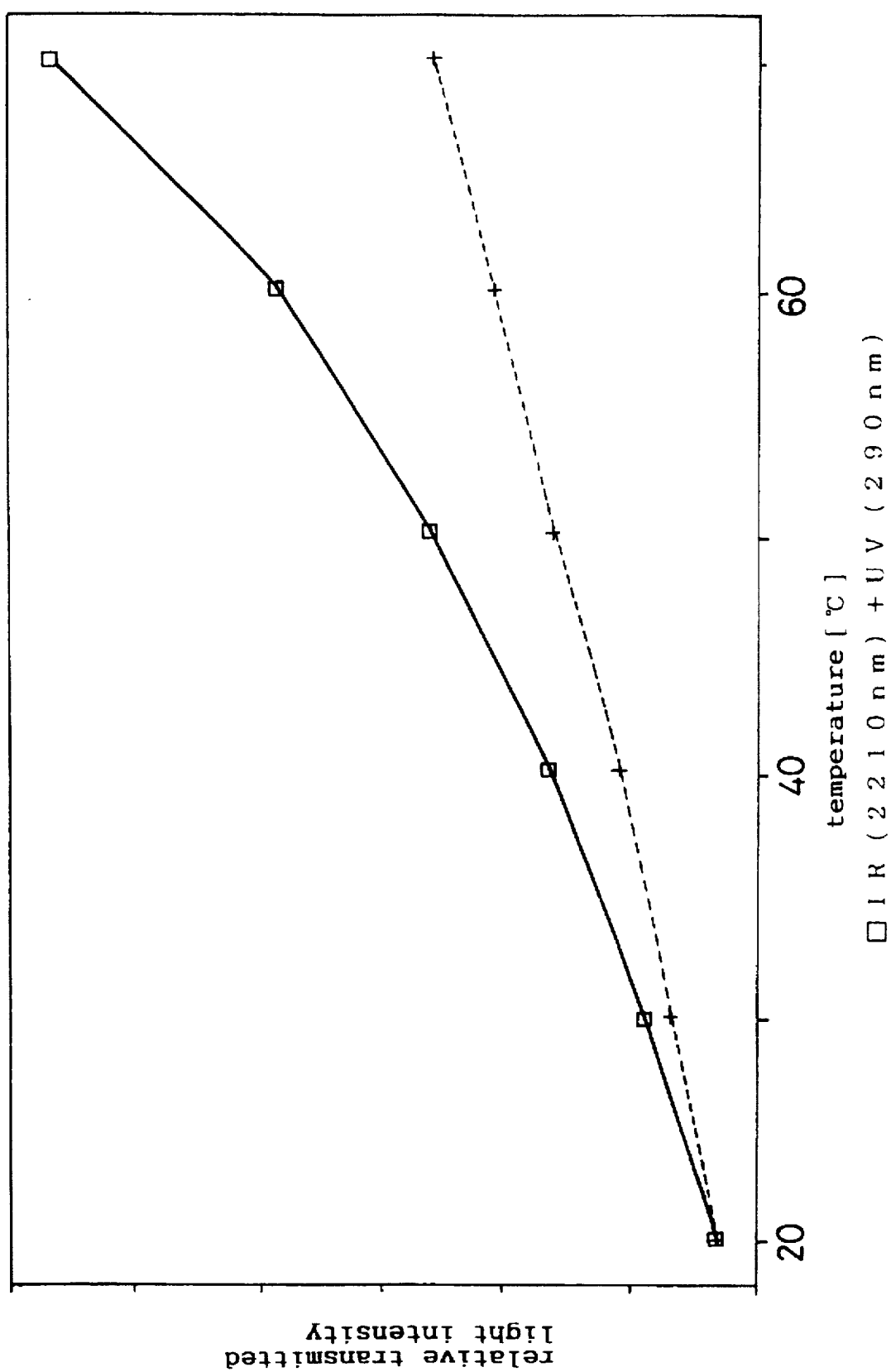
FIG. 3 is a graph showing an example of calibration curve for the first embodiment.

At step P1, only deionized water is supplied to the treating bath 1 through the deionized water supply pipe 3, to the extent of filling the main treating vessel 1a and overflow vessel 1b. Then, the deionized water is circulated by the pump 11. Next, the calibration curve data measuring unit 33 controls the temperature control unit 32 to vary the temperature of the deionized water within a predetermined range, and acquires transmitted light intensities of the deionized water (solvent) at varied temperatures from the transmitted light intensity measuring unit 31 (step P2). At step P3, calibration curve data showing the relationship between temperatures and transmitted light intensities of the deionized water measured at step P2 are stored in the calibration curve data storage 34. FIG. 3 shows an example of calibration curve data stored. In the example shown in FIG. 3, the calibration curve data are obtained by dividing the light transmitted through the sample flow cell 19 into ultraviolet light (wavelength: 290 nm) and infrared light (wavelength: 2210 nm). In FIG. 3, the horizontal axis represents the temperatures of the deionized water, while the vertical axis represents the transmitted light intensities of ultraviolet light and infrared light. Both curves describe lines rising rightward as clearly shown in FIG. 3. It means that the transmitted light intensities of ultraviolet light and infrared light increase with the temperature of the deionized water.

At step P4, the treating solution is adjusted to a predetermined concentration "c" by the standard treating solution adjusting device (not shown). This treating solution is called the standard treating solution. After draining the deionized water supplied at step P1, the standard treating solution is supplied to the treating bath 1 to the extent of filling the main treating vessel 1a and overflow vessel 1b, and is circulated by the pump 11. Further, the standard treating solution is heated to a predetermined temperature "te" by means of the temperature controller 32, heater 13 and temperature sensor 15. In this state, the transmitted light intensity measuring unit 31 causes the optical path switcher control unit 39 to couple the optical path switcher 24 to the sample flow cell 19, measures transmitted light intensity, and transfers the measured intensity as the standard transmitted light intensity $I_R$ to the transmittance computing unit 36. The temperature control unit 32 measures the temperature of the standard treating solution based on an output of the temperature sensor 15. The measured temperature "tm" (substantially the same as predetermined temperature "te") is communicated to the correction factor computing unit 35 (step P5). At step P6, transmitted light intensity measuring unit 31 causes the optical path switcher 24 to be coupled to the reference cell 23, measures transmitted light intensity, and communicates the measured intensity as the reference transmitted light intensity $I_V$ to the transmittance computing unit 36.

At step P7, the correction factor computing unit 35 computes the correction factor K. The correction factor computing unit 35 first inputs measured temperature "tm" of the standard treating solution to the calibration curve data storage 34. The calibration curve data storage 34 determines a transmitted light intensity of the deionized water corresponding to the measured temperature "tm" from the calibration curve data stored therein, and returns this transmitted light intensity to the correction factor computing unit 35. This transmitted light intensity corresponds to the transmitted light intensity where the temperature of the deionized water filling the reference cell 23 equals measured temperature "tm" of the standard treating solution. This transmitted light intensity acts as the estimated transmitted light intensity $I_F$. The correction factor computing unit 35 computes the correction factor K $(=I_V/I_F)$ based on the ratio between reference transmitted light intensity $I_V$ measured at step P6 and estimated transmitted light intensity $I_F$.

At step P8, the transmittance computing unit 36 computes the transmittance of the standard treating solution based on standard transmitted light intensity $I_R$ measured at step P5, reference transmitted light intensity $I_V$ measured at step P6, and correction factor K computed at step P7. This transmittance is the transmittance at the measured temperature "tm" (substantially the same as predetermined temperature "te") of the standard treating solution, which acts as standard transmittance $T_R$ $(=K \cdot I_R/I_V)$. The standard transmittance $T_R$ thus obtained is stored in the transmittance computing unit 36.

As described above, the reference transmitted light intensity $I_V$ is corrected with measured temperature "tm" of the standard treating solution to obtain standard transmittance $T_R$. Thus, the standard transmittance $T_R$ can be obtained accurately without cooling the standard treating solution to the temperature of the deionized water filling the reference cell 23.

Figure 4:
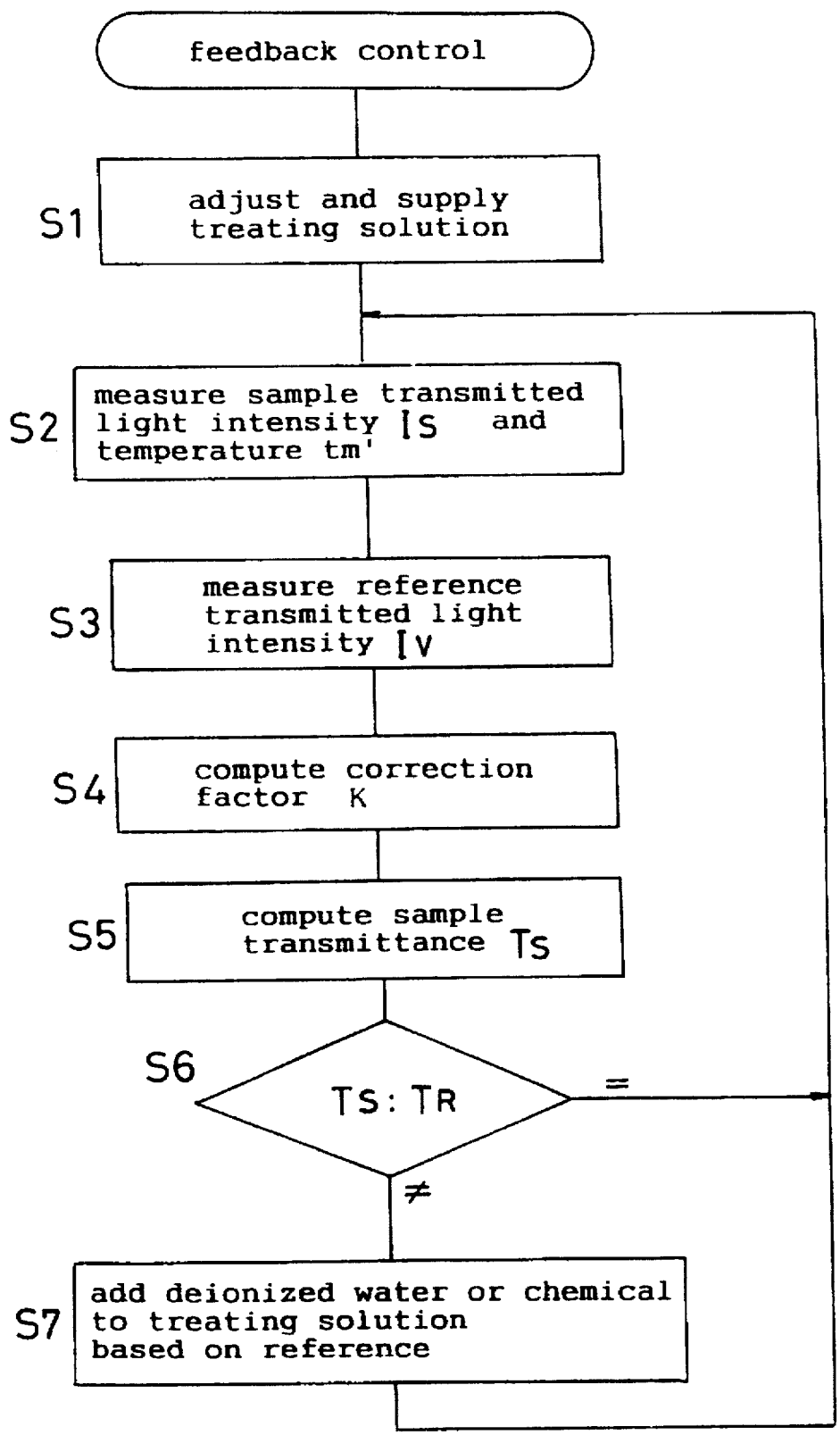
FIG. 4 is a flowchart of a feedback control for the first embodiment.

A feedback control sequence will be described next with reference to FIG. 4. This feedback control sequence corresponds to the feedback control process of the present invention.

At step S1, the supply control unit 38 controls the flow control valve V1 for deionized water and the flow control valve V2 for the chemical, to supply the chemical and deionized water to the treating bath 1 at a ratio for substantially attaining predetermined concentration "c". After the treating solution fills the overflow vessel 1b, the pump 11 is driven to circulate the treating solution through the supply pipe 9, and the temperature control unit 32 adjusts the treating solution to predetermined temperature "te".

At step S2, the transmitted light intensity measuring unit 31 causes the optical path switcher 24 to be coupled to the sample flow cell 19, measures transmitted light intensity through the sample flow cell 19, and outputs this transmitted light intensity as sample transmitted light intensity $I_S$ to the transmittance computing unit 36. At the same time, the temperature control unit 32 measures the temperature of the treating solution, and communicates measured temperature "tm'" (substantially the same as predetermined temperature "te") to the correction factor computing unit 35. Next, the transmitted light intensity measuring unit 31 causes the optical path switcher 24 to be coupled to the reference cell 23, measures reference transmitted light intensity $I_V$, and outputs it to the transmittance computing unit 36 (step S3).

At step S4, the correction factor computing unit 35 computes correction factor K. The correction factor computing unit 35 sends the measured temperature "tm'" (measured at step S2, and substantially the same as predetermined temperature "te") of the treating solution to the calibration curve data storage 34. The calibration curve data storage 34 determines a transmitted light intensity corresponding to measured temperature "tm'" with reference to the calibration curve data stored therein, and returns the transmitted light intensity to the correction factor computing unit 35. This transmitted light intensity corresponds to the transmitted light intensity where the temperature of the deionized water filling the reference cell 23 equals measured temperature "tm'" of the standard treating solution. This transmitted light intensity acts as estimated transmitted light intensity $I_F$. The correction factor K $(=I_V/I_F)$ is computed based on the ratio between reference transmitted light intensity $I_V$ measured at step S3 and estimated transmitted light intensity $I_F$.

At step S5, sample transmittance $T_S$ $(=K \cdot I_S/I_V)$ is computed based on the sample transmitted light intensity $I_S$, the reference transmitted light intensity $I_V$ and the correction factor K.

As described above, the reference transmitted light intensity $I_V$ is corrected with measured temperature "tm'" of the treating solution to obtain the sample transmittance $T_S$. Thus, the sample transmittance $T_S$ is obtained accurately without cooling the treating solution, for use in treatment of wafers, to the temperature of the deionized water filling the reference cell 23.

At step S6, standard transmittance $T_R$ and sample transmittance $T_S$ are compared with each other. If transmittance $T_R$ and transmittance $T_S$ are equal (i.e. the concentration of the treating solution for actual use in treatment of wafers is the same as that of the standard treating solution), the operation returns to step S2. If transmittance $T_R$ and transmittance $T_S$ are different from each other (i.e. the concentration of the treating solution for actual use in treatment of wafers is different from that of the standard treating solution), the operation proceeds to step S7. At step S7, either the chemical or deionized water is supplemented to the treating solution according to the difference between standard transmittance $T_R$ and sample transmittance $T_S$. Specifically, transmittance $T_R$ and transmittance $T_S$ are sent from the transmittance computing unit 36 to the feedback control unit 37. The feedback control unit 37 outputs a control signal corresponding to the difference between $T_S$ and $T_R$, to the supply control unit 38. The supply control unit 38 adjusts the flow control valve V1 or V2 by an amount corresponding to the control signal. Then, the operation returns to step S2 to repeat the above sequence.

By repeating steps S2 through S7, the concentration of the treating solution for actual use in treatment of wafers is controlled to attain a predetermined value, in accordance with the difference between standard transmittance $T_R$ relating to the concentration of the standard treating solution and sample transmittance $T_S$ relating to the concentration of the treating solution for actual use in treatment of wafers. That is, the concentration control is effected based on the difference between the two types of transmittance relating to concentrations, without computing the concentrations, whereby the amount of required computation is reduced. Further, the influence of temperature is eliminated to bring the concentration of the treating solution for actual use in treatment of wafers into agreement with the concentration of the standard treating solution accurately and speedily.

B. According to the Second Embodiment (Substrate Treating Apparatus Utilizing the Second Aspect of the Invention)

Figure 5:
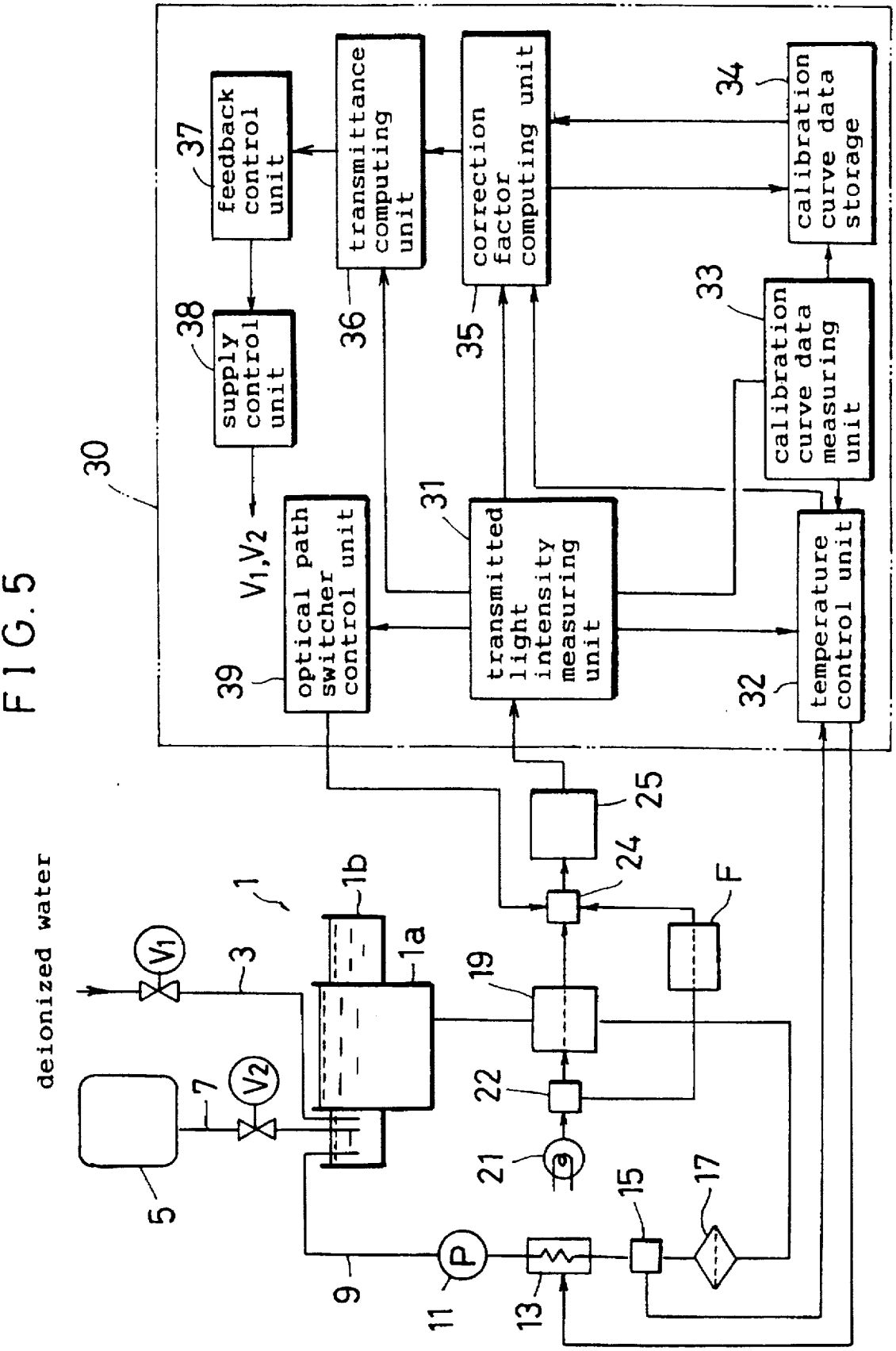
FIG. 5 is a schematic of a substrate treating apparatus constructed according to a second embodiment of this invention.

FIG. 5 is a schematic of a substrate treating apparatus according to a second embodiment of the present invention wherein, like reference numerals are used to identify like parts that are also found in the first embodiment, and will not be described again.

As in the first embodiment, light from the light source 21, such as a halogen lamp, is divided by the light divider 22 to travel in two directions. One divided part of the light irradiates the sample flow cell 19. In the first embodiment, the other part of the light irradiates the reference cell 23, while in this embodiment, the other part irradiates a filter that is provided to reduce incident light from the light source 21. Filter F has a fixed reduction rate that is preferably of such a value as to reduce the light to a level close to the intensity of light having passed through the sample flow cell 19. This filter F is also provided to diminish an error in the calculation described hereinafter. Where the influence of such error is negligible, the light emitted by the light source 22 may be applied directly to the optical path switcher 24 without passing through the filter F. The intensity of light having passed through the filter F, or the intensity of light source 21 where the filter F is not provided, relates to the luminous intensity of light source 21, and corresponds to the source-related light intensity.

The light having passed through the sample flow cell 19 or filter F is converted by the optical detector 25 into a signal corresponding to light intensity, which signal is applied to the concentration controller 30.

While circulating a "standard treating solution" adjusted to a predetermined concentration by the standard treating solution adjusting device (not shown) through the treating solution supply pipe 9, transmitted light intensity measuring unit 31 measures the intensity of light transmitted through the sample flow cell 19 (standard transmitted light intensity $I_R$) of this solution adjusted to a predetermined temperature by using the temperature control unit 32, heater 13 and temperature sensor 15. Along with this measurement, the transmitted light intensity measuring unit 31 causes the optical path switcher control unit 39 to couple the optical path switcher 24 to the filter F, and measures reduced source light intensity $I_O'$ corresponding to the source-related light intensity. Then, the standard treating solution circulating through the supply pipe 9 is purged via a drain (not shown), and the flow control valve V1 is adjusted to circulate deionized water through the supply pipe 9. The deionized water is maintained at a predetermined temperature by using the temperature control unit 32, heater 13 and temperature sensor 15. In this condition, the transmitted light intensity measuring unit 31 measures the transmitted light intensity (reference transmitted light intensity $I_V$) through the sample flow cell 19, and measures reduced source light intensity $I_O'$ by causing the switcher control unit 39 to couple the optical path switcher 24 to the filter F.

Further, while circulating a treating solution adjusted to the same temperature and intended to be adjusted to the same concentration as that of the standard treating solution, the transmitted light intensity measuring unit 31 measures its transmitted light intensity (sample transmitted light intensity $I_S$). Then, the transmitted light intensity measuring unit 31 causes the optical path switcher 24 to be coupled to the filter F, and measures reduced source light intensity $I_O'$. The transmitted light intensities $I_R$, $I_V$ and $I_S$ measured by the transmitted light intensity measuring unit 31 are applied to the transmittance computing unit 36 as ratios of transmitted light intensity/reduced source light intensity unit 36. The ratio between standard transmitted light intensity $I_R$ and reduced source light intensity $I_O'$ is regarded herein as standard transmitted light intensity ratio $R_R$ ($=I_R/I_O'$); and the ratio between reference transmitted light intensity $I_V$ and reduced source light intensity $I_O'$ is regarded as reference transmitted light intensity ratio $R_V$ ($=I_V/I_O'$); and the ratio between sample transmitted light intensity $I_S$ and reduced source light intensity $I_O'$ is regarded as sample transmitted light intensity ratio $R_S$ ($=I_S/I_O'$).

The calibration curve data measuring unit 33, in the condition in which only deionized water flows through the sample flow cell 19, acquires transmitted light intensities from the transmitted light intensity measuring unit 31 while varying the temperature of the deionized water through the temperature control unit 32. The calibration curve data measuring unit 33 acquires also the reduced source light intensity from the transmitted light intensity measuring unit 31 by causing the optical path switcher 24 to be coupled to the filter F. Calibration curve data showing relationship between the temperatures and transmitted light intensity ratios (transmitted light intensity/reduced source light intensity) measured as above are stored in the calibration curve data storage 34.

The correction factor computing unit 35 computes estimated transmitted light intensity $R_F$ based on the temperature of the standard treating solution or of the treating solution for use in treatment of wafers, and the calibration curve data stored in the calibration curve data storage 34. The estimated transmitted light intensity $R_F$ corresponds to the reference transmitted light intensity ratio ($I_F/I_O'$) which is the ratio between reference transmitted light intensity $I_F$ and reduced source light intensity $I_O'$ where the deionized water filling the sample flow cell 19 is at the same temperature as the standard treating solution or the treating solution for use in treatment of wafers. The correction factor computing unit 35 then computes correction factor K based on the ratio between reference transmitted light intensity $R_V$ and estimated transmitted light intensity $R_F$.

The transmittance computing unit 36 computes the transmittance of the standard treating solution (standard transmittance $T_R$) based on standard transmitted light intensity $R_R$, reference transmitted light intensity $R_V$, and correction factor K, and computes the transmittance of the treating solution for use in treatment of wafers (sample transmittance $T_S$) based on sample transmitted light intensity $R_S$, reference transmitted light intensity $R_V$ and correction factor K.

The feedback control unit 37 receives standard transmittance $T_R$ and sample transmittance $T_S$ from the transmittance computing unit 36, and outputs to the supply control unit 38 a control signal reflecting a difference between the standard transmittance $T_R$ and the sample transmittance $T_S$. The supply control unit 38 effects an appropriate adjustment of the flow control valve V1 on the deionized water supply pipe 3 or the flow control valve V2 on the chemical supply pipe 7 to adjust the concentration of the treating solution for use in treatment of wafers.

The sequence that is executed first is a standard setting sequence (corresponding to the standard setting process) which will be described now with reference to the flowchart shown in FIG. 6.

At step P1, only deionized water is supplied to the treating bath 1 through the deionized water supply pipe 3, to the extent of filling the main treating vessel 1a and overflow vessel 1b. Then, the deionized water is circulated by the pump 11. Next, the calibration curve data measuring unit 33 controls the temperature control unit 32 to vary the temperature of the deionized water within a predetermined range. At this time unit 33 also acquires transmitted light intensities at varied temperatures from the transmitted light intensity measuring unit 31. Then, the calibration curve data measuring unit 33 causes the optical path switcher 24 to be coupled to the filter F, and acquires reduced source light intensities at the varied temperatures from the transmitted light intensity measuring unit 31 (step P2).

Figure 7:
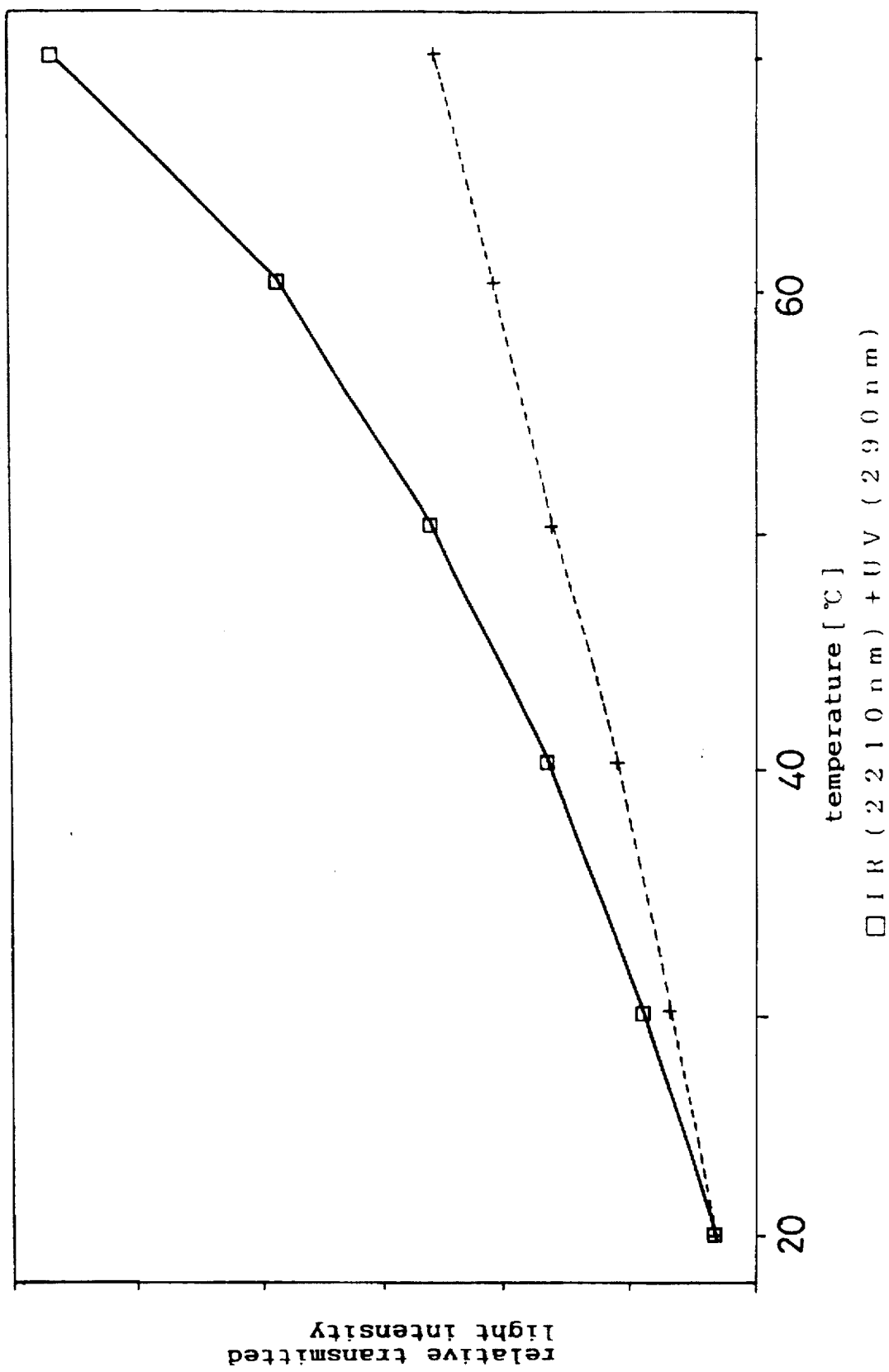
FIG. 7 is a graph showing an example of calibration curve for the second embodiment.

At step P3, calibration curve data showing the relationship between the temperatures and transmitted light intensity ratios (transmitted light intensity/reduced source light intensity) measured at step P2 are stored in the calibration curve data storage 34. FIG. 7 shows an example of calibration curve data that is stored in unit 34. In the example shown in FIG. 7, the calibration curve data are obtained by dividing the light transmitted through the sample flow cell 19 into ultraviolet light and infrared light as in the first embodiment.

At step P4, the standard treating solution is prepared and heated to predetermined temperature "te" as in the first embodiment. In this state, the transmitted light intensity measuring unit 31 measures transmitted light intensity, and the measured intensity is outputted to the transmittance computing unit 36 as standard transmitted light intensity $I_R$. Then, the transmitted light intensity measuring unit 31 causes the optical path switcher 24 to be coupled to the filter F, measures reduced source light intensity $I_O'$, and outputs it to the transmittance computing unit 36. The temperature control unit 32 measures the temperature of the standard treating solution, and outputs the measured temperature "tm" (substantially the same as predetermined temperature "te") to the correction factor computing unit 35 (step P5).

At step P6, the standard treating solution circulating through the supply pipe 9 is purged via the drain (not shown), and the deionized water adjusted to the predetermined temperature by the temperature control unit 32 is circulated through the supply pipe 9. That is, the deionized water maintained at the predetermined temperature is caused to flow through the sample flow cell 19.

At step P7, the transmitted light intensity measuring unit 31 measures transmitted light intensities by causing the optical path switcher 24 to be coupled to the sample flow cell 19 and then to the filter F. These light intensities are outputted as reference transmitted light intensity $I_V$ and reduced source light intensity $I_O'$ to the transmittance computing unit 36.

At step P8, the correction factor computing unit 35 computes correction factor K. The correction factor computing unit 35 first inputs measured temperature "tm" of the standard treating solution (measured at step P5) to the calibration curve data storage 34. The calibration curve data storage 34 determines a transmitted light intensity ratio corresponding to measured temperature "tm" based on the calibration curve data ((transmitted light intensities/reduced source light intensities)–temperatures) stored therein, and outputs this ratio to the correction factor computing unit 35. This transmitted light intensity ratio corresponds to the transmitted light intensity ratio acquired where the temperature of the deionized water circulating through the sample flow cell 19 equals measured temperature "tm" of the standard treating solution. This transmitted light intensity ratio acts as estimated transmitted light intensity $R_F$ (estimated light intensity $I_F$/reduced source light intensity $I_O'$). The correction factor computing unit 35 computes correction factor K ($=I_V/I_F$) based on the ratio between reference transmitted light intensity $R_V$ ($I_V/I_O'$) (measured at step P7) and estimated transmitted light intensity $R_F$ ($=I_F/I_O'$). With the reduced source light intensity $I_O'$ in the two ratios canceling each other, this correction factor K corresponds to a ratio between reference transmitted light intensity $I_V$ and estimated transmitted light intensity $I_F$, as in the first embodiment.

At step P9, the transmittance computing unit 36 computes the transmittance of the standard treating solution based on standard transmitted light intensity $R_R$ ($I_R/I_O'$) measured at step P5, reference transmitted light intensity $R_V$ ($I_V/I_O'$) measured at step P7, and correction factor K computed at step P8. This transmittance is the transmittance of the standard treating solution at measured temperature "tm" (substantially the same as predetermined temperature "te"), which acts as standard transmittance $T_R$ ($=K \cdot R_R/R_V = K \cdot (I_R/I_O')/(I_V/I_O') = K \cdot I_R/I_V$). This standard transmittance $T_R$ is expressed by an equation similar to that used in the first embodiment, and is stored in the transmittance computing unit 36.

As described above, the reference transmitted light intensity ratio $R_V$ based on the temperature different from that of the standard treating solution is corrected with measured temperature "tm" of the standard treating solution to obtain standard transmittance $T_R$. Thus, standard transmittance $T_R$ is obtained accurately without cooling the standard treating solution to the temperature of the deionized water circulating through the sample flow cell 19. Furthermore, according to this embodiment, standard transmittance $T_R$ is obtained without using the reference cell 23 used in the first embodiment. Moreover, the reduced source light intensity is measured along with the transmitted light intensities, and various values are computed based on ratios therebetween. These ratios are substantially invariable with variations in the luminous intensity of light source 21. Thus, standard transmittance $T_R$ is determined accurately.

Figure 8:
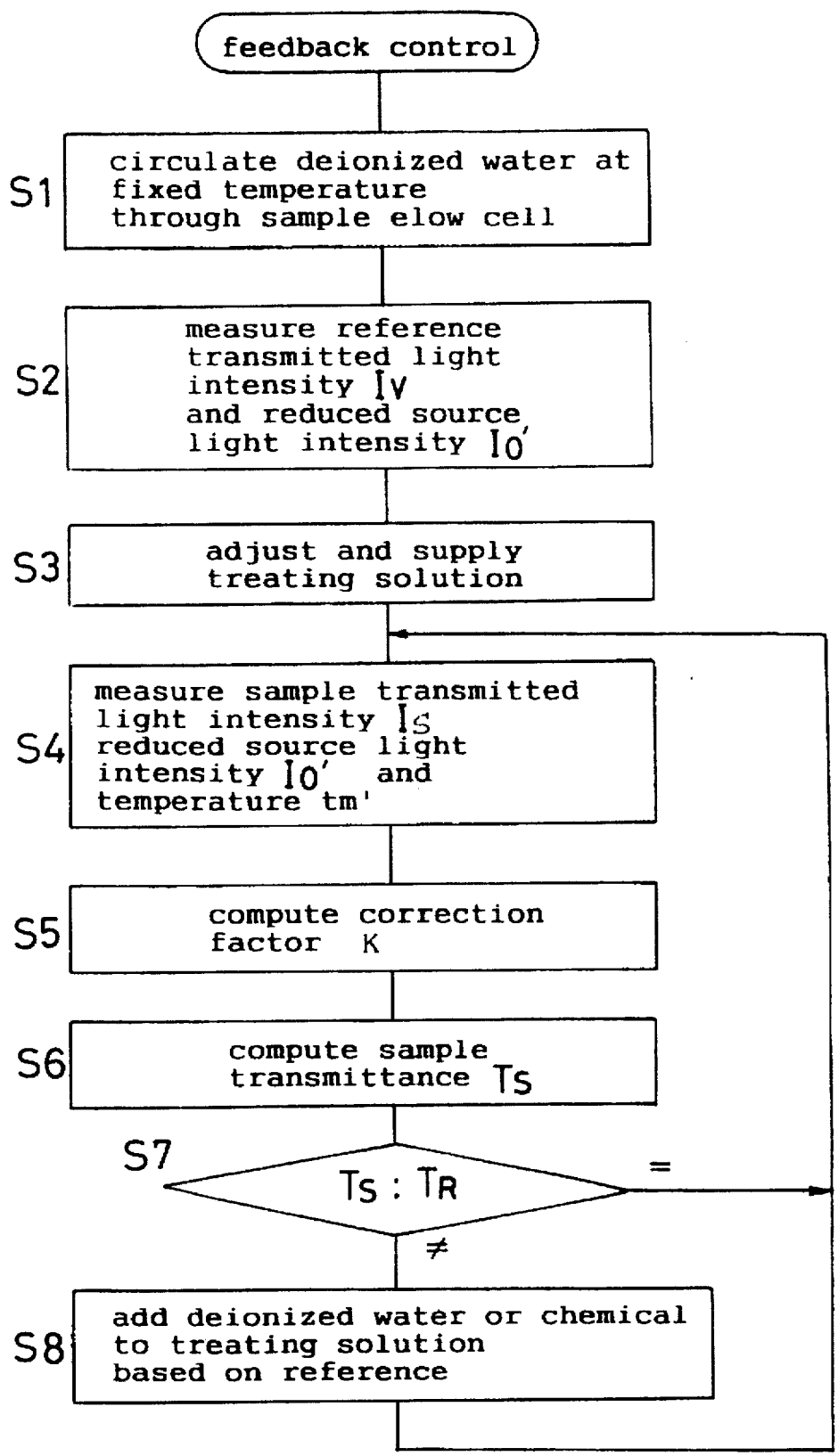
FIG. 8 is flowchart of a feedback control for the second embodiment.

A feedback control sequence (corresponding to the feedback control process) will be described now with reference to FIG. 8.

Figure 6:
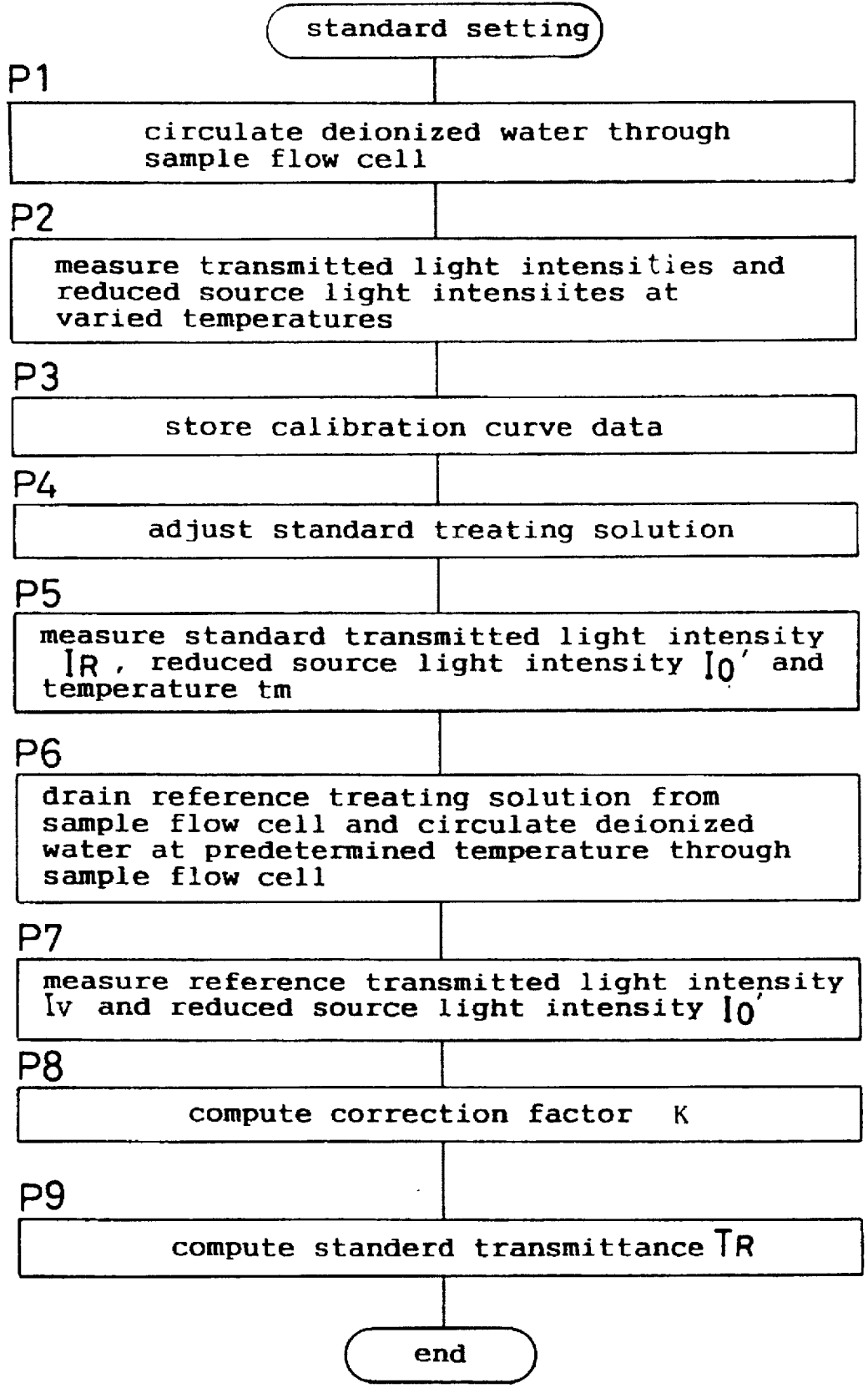
FIG. 6 is a flowchart of a standard setting process for the second embodiment.

At step S1, as at step P6 of the standard setting sequence shown in FIG. 6, the deionized water maintained at the predetermined temperature is circulated through the sample flow cell 19. Then, as at step P7 of the standard setting sequence, the transmitted light intensity measuring unit 31 measures reference transmitted light intensity $I_V$ and reduced source light intensity $I_O'$ in this condition (step S2). These intensities are outputted as reference transmitted light intensity ratio $R_V$ ($I_V/I_O'$).

At step S3, as at step S1 in the first embodiment (FIG. 4), the chemical and deionized water are supplied substantially in the predetermined concentration "c" to the treating bath 1. The temperature control unit 32 adjusts the solution to predetermined temperature "te".

At step S4, the transmitted light intensity measuring unit 31 measures transmitted light intensities by causing the optical path switcher 24 to be coupled to the sample flow cell 19 and then to the filter F. These light intensities, i.e. sample transmitted light intensity $I_S$ and reduced source light intensity $I_O'$, are outputted as sample transmitted light intensity ratio $R_S$ ($=I_S/I_O'$) to the correction factor computing unit 35. Further, the temperature control unit 32 measures the temperature of the treating solution, and outputs the measured temperature "tm'" (substantially the same as predetermined temperature "te") to the correction factor computing unit 35.

At step S5, the correction factor computing unit 35 computes correction factor K. The correction factor computing unit 35 inputs measured temperature "tm'" (measured at step S4, and substantially the same as predetermined temperature "te") of the treating solution to the calibration curve data storage 34. The calibration curve data storage 34 determines a transmitted light intensity ratio corresponding to measured temperature "tm'" from the calibration curve data stored therein, and outputs the transmitted light intensity ratio to the correction factor computing unit 35. This transmitted light intensity ratio corresponds to the transmitted light intensity where the temperature of the deionized water circulating through the reference flow cell 19 equals measured temperature "tm'" of the treating solution. This transmitted light intensity ratio acts as estimated transmitted light intensity ratio $R_F$ (=$I_F/I_O'$), and correction factor K (=$I_V/I_F$) is computed based on the ratio between reference transmitted light intensity $R_V$ (=$I_V/I_O'$) measured at step S2 and estimated transmitted light intensity ratio $R_F$.

At step S6, sample transmittance $T_S$ (=$K \cdot R_S/R_V$=$K \cdot (I_S/I_O')/(I_V/I_O')$=$K \cdot I_S/I_V$) is computed based on sample transmitted light intensity $R_S$, reference transmitted light intensity $R_V$ and correction factor K. The sample transmittance $T_S$ is expressed by an equation similar to that in the first embodiment, and is stored in the transmittance computing unit 36. In this way, the reference transmitted light intensity $R_V$ is corrected with measured temperature "tm'" of the treating solution to obtain sample transmittance $T_S$. Thus, sample transmittance $T_S$ is obtained accurately without cooling the treating solution to the temperature of the deionized water circulating through the sampling flow cell 19. The respective transmitted light intensities are computed from their ratios to the reduced source light intensities relating to the luminous intensities of the light source. These ratios are substantially invariable despite variations in the luminous intensity of light source 21. Thus, sample transmittance $T_S$ is obtained accurately.

At step S7, as in the first embodiment, standard transmittance $T_R$ and sample transmittance $T_S$ are compared with each other. If transmittance $T_R$ and transmittance $T_S$ are equal (i.e. the concentration of the treating solution for actual use in treatment of wafers is the same as that of the standard treating solution), the operation returns to step S4. If transmittance $T_R$ and transmittance $T_S$ are different from each other (i.e. the concentration of the treating solution for actual use in treatment of wafers is different from that of the standard treating solution), the operation proceeds to step S8. At step S8, either the chemical or deionized water is supplemented to the treating solution according to the difference between standard transmittance $T_R$ and sample transmittance $T_S$. Then, the operation returns to step S4 to repeat steps S4 through S8.

By repeating steps S4 through S8, the concentration of the treating solution for actual use in treatment of wafers is controlled with high precision, in accordance with the difference between standard transmittance $T_R$ and sample transmittance $T_S$ relating to concentrations, as in the first embodiment. Further, since standard transmittance $T_R$ and sample transmittance $T_S$ are computed based on their ratios to the reduced source light intensity $I_O'$ which is the source-related light intensity, transmittance values are obtained accurately even with variations in the luminous intensity of light source 21. This assures that concentration control will be accurate over a long period of time.

In the first embodiment described hereinbefore, the light intensity relating to the luminous intensity of light source 21 is not measured. However, the reference cell 23 may include a device for measuring the luminous intensity of light source 21. Such a device may be provided for filter F which reduces the light from the light source 21 as in the second embodiment (or directly, without reducing the light with filter F). The light divider 22 may divide the light in two or three directions, with the optical path switcher 24 having two or three inputs. Then, as in the second embodiment, calibration curve data represent transmitted light intensity ratios (transmitted light intensity/reduced source light intensity)—temperatures, with each transmitted light intensity in the form of its ratio to the reduced source light intensity.

Figure 9:
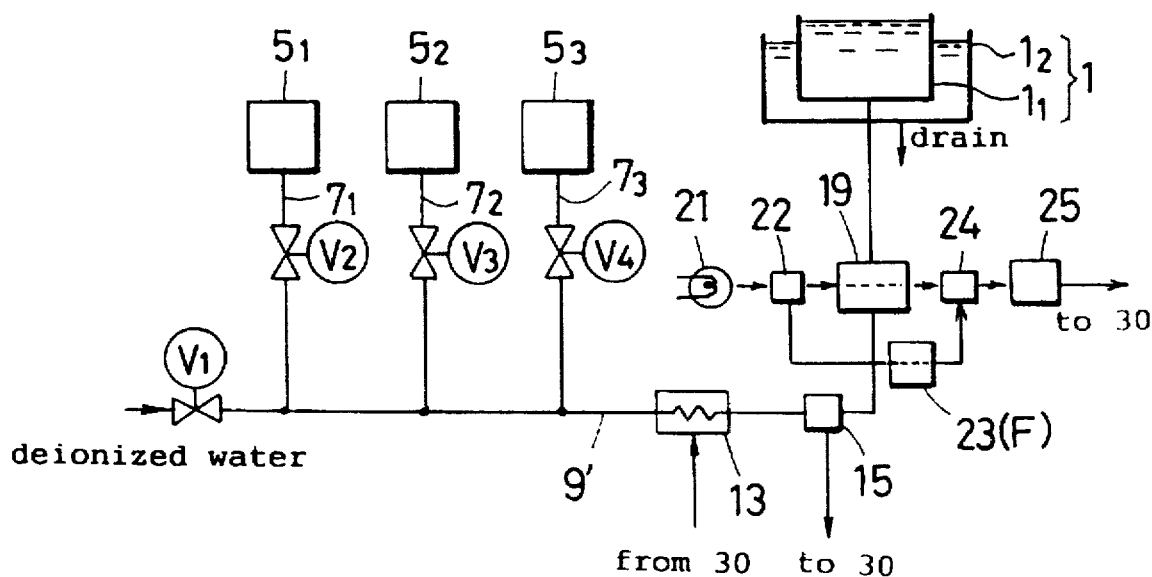
FIG. 9 is a schematic of a modified substrate treating apparatus constructed according to the second embodiment.

The present invention is not limited to the substrate treating apparatus shown in FIG. 1 (first embodiment) or FIG. 5 (second embodiment), but is applicable also to a substrate treating apparatus as shown in FIG. 9. In the first and second embodiments shown in FIGS. 1 and 5, the treating solution is circulated through the treating solution supply pipe 9. The substrate treating apparatus of FIG. 9 is differently constructed as follows.

Deionized water is supplied to treating solution supply pipe 9' through a flow control valve V1. Further, a plurality of different chemicals are supplied thereto from a plurality of chemical tanks $5_1$–$5_3$ through respective flow control valves V2–V4 and respective chemical pipes $7_1$–$7_3$, to prepare a treating solution at a predetermined mixing ratio. The treating solution prepared is adjusted to a predetermined temperature by a heater 13 and a temperature sensor 15 mounted on the treating solution supply pipe 9'. The treating solution adjusted to a predetermined concentration and temperature is supplied to a treating bath 1. Concentration control may be effected accurately and with excellent responsivity by combining the substrate treating apparatus of FIG. 9 with the concentration controller 30 described hereinbefore.

Some kinds of treating solutions need to have transmitted light intensities measured in a plurality of wavelength bands. Treating solution including ammonia and hydrogen peroxide, for example, has wide variations in the transmitted light intensity due to the concentration of ammonia in the infrared band, and wide variations in the transmitted light intensity due to the concentration of hydrogen peroxide in the ultraviolet band. Preferably, therefore, an optical detector as shown in FIG. 10 should be used to measure the transmitted light intensity of such treating solution, and control its concentration based thereon.

Specifically, the light transmitted through the sample flow cell 19 is separated by an optical path switcher 24' into ultraviolet light UV and infrared light $I_R$ to enter an ultraviolet detector $25b_1$ and an infrared detector $25b_2$, respectively. The separation into ultraviolet light and infrared light is effected by a combination of a dichroic mirror, an ultraviolet band-pass filter, an infrared band-pass filter and the like. The optical path switcher 24' also has a function to switch an optical path between sample flow cell 19 and reference cell 23 (or filter F) as in the construction shown in FIG. 1 (or FIG. 5).

Figure 10:
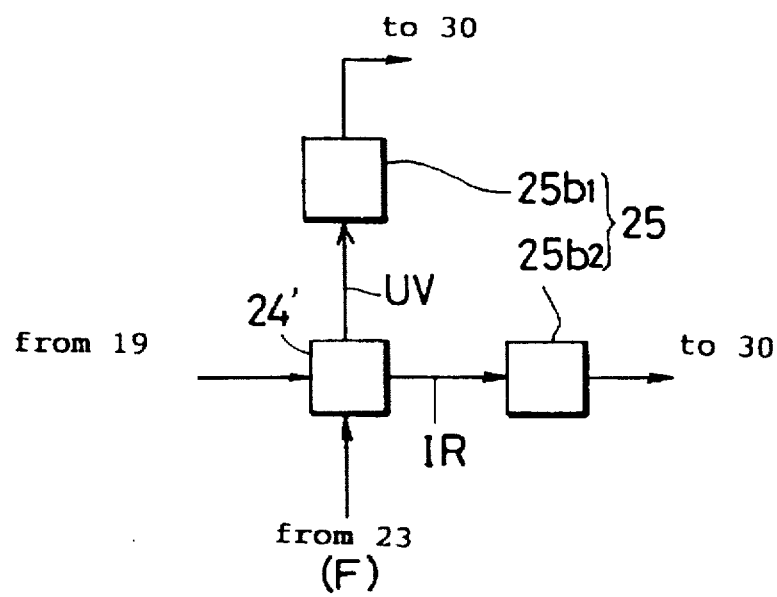
FIG. 10 is a block diagram of a modified optical detector.

In this construction of FIGS. 9 and 10, calibration curve data are computed based on each of the ultraviolet light and infrared light. Further, standard transmitted light intensities $I_{R(UV)}$ and $I_{R(IR)}$, reference transmitted light intensities $I_{V(UV)}$ and $I_{V(IR)}$ and the like are measured to obtain standard transmittances $T_{R(UV)}$ and $T_{R(IR)}$ and sample transmittances $T_{S(UV)}$ and $T_{S(IR)}$. Hydrogen peroxide (or deionized water) may be supplemented to the treating solution based on a difference between standard transmittance $T_{R(UV)}$ and sample transmittance $T_{S(UV)}$ relating to the ultraviolet light. Ammonia (or deionized water) may be supplemented to the treating solution based on a difference between standard transmittance and $T_{R(IR)}$ and sample transmittance $T_{S(IR)}$ relating to the infrared light.

Instead of supplementing a chemical or deionized water to the treating solution in order to adjust the concentration thereof, a gas corresponding to the chemical may be mixed into the treating solution in a way that the gas is completely dissolved therein. If, for example, the treating solution contains hydrogen chloride, then hydrogen chloride gas is added to the treating solution. Supplementing of the treating solution with a gas corresponding to a chemical provides the advantage of avoiding an increase in liquid quantity of the treating solution.

The first and second embodiments exemplify deionized water as a solvent, but the herein invention is not limited thereto. For example, in a cleaning treatment using organic solvent, a solvent suited for the treatment (e.g. acetone or isopropyl alcohol) may be employed.

C. Transmitted Light Measuring Flow Cell Suited for Use in Substrate Treating Apparatus Generally, a transmitted light measuring flow cell acting as each of the sampling flow cell and reference cell in the apparatus described hereinbefore includes an opposed pair of light transmitting elements formed of quartz or sapphire ($Al_2O_3$) and spaced from each other by a predetermined distance (cell length). Light enters the flow cell through one of the transmitting elements to irradiate an object fluid flowing between the pair of transmitting elements. A light intensity emerges through the other transmitting element to be measured.

The transmitted light measuring flow cell constructed as above has a number of drawbacks, namely, where the object fluid (treating solution) contains a highly corrosive chemical such as hydrofluoric acid (HF), surfaces of the light transmitting elements formed of quartz or sapphire become corroded. This corrosion increases the predetermined distance (cell length) between the opposed transmitting elements with the passage of time. As a result, the intensity of light passing through the object fluid gradually decreases.

Where the transmitting elements are formed of sapphire, corrosion caused by the chemical gives rise to the additional problem that aluminum in sapphire is dissolved into the object fluid to contaminate the latter. Particularly in an apparatus for treating semiconductor wafers, the concentration of the object fluid acting as a treating solution is adjusted for surface treatment, such as cleaning treatment, of semiconductor wafers. The dissolution of aluminum or other metal into the object fluid acting as the treating solution poses a serious problem of lowering yield of semiconductor wafers in mass production.

A flow cell for measuring transmitted light according to the present invention (to be described in detail, hereinafter), which prevents corrosion of the light transmitting elements to stabilize the cell length over a long period of time and to avoid contamination of an object fluid.

Figure 11:
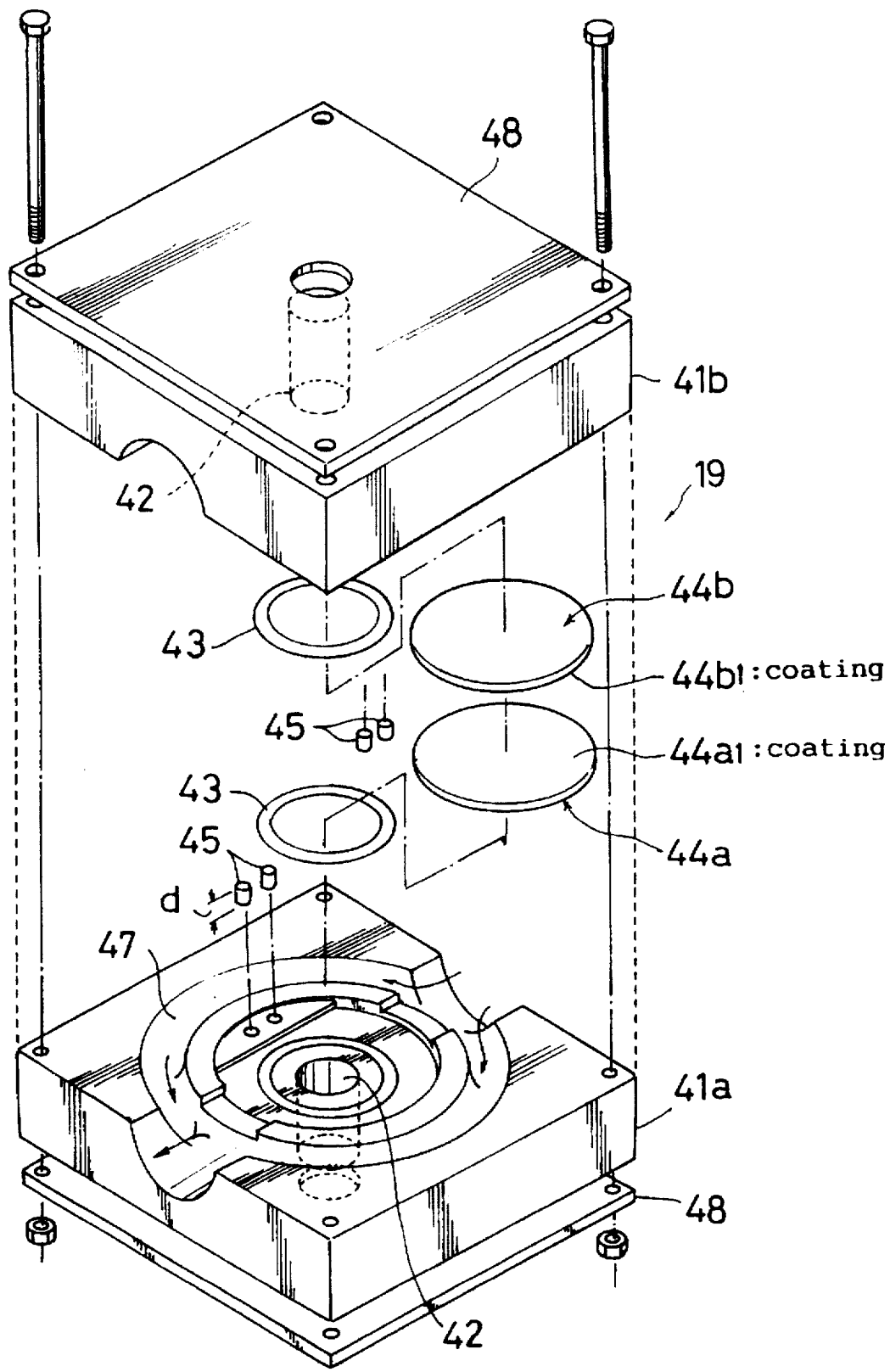
FIG. 11 is an exploded perspective of an example of a flow cell for measuring transmitted light.
Figure 12:
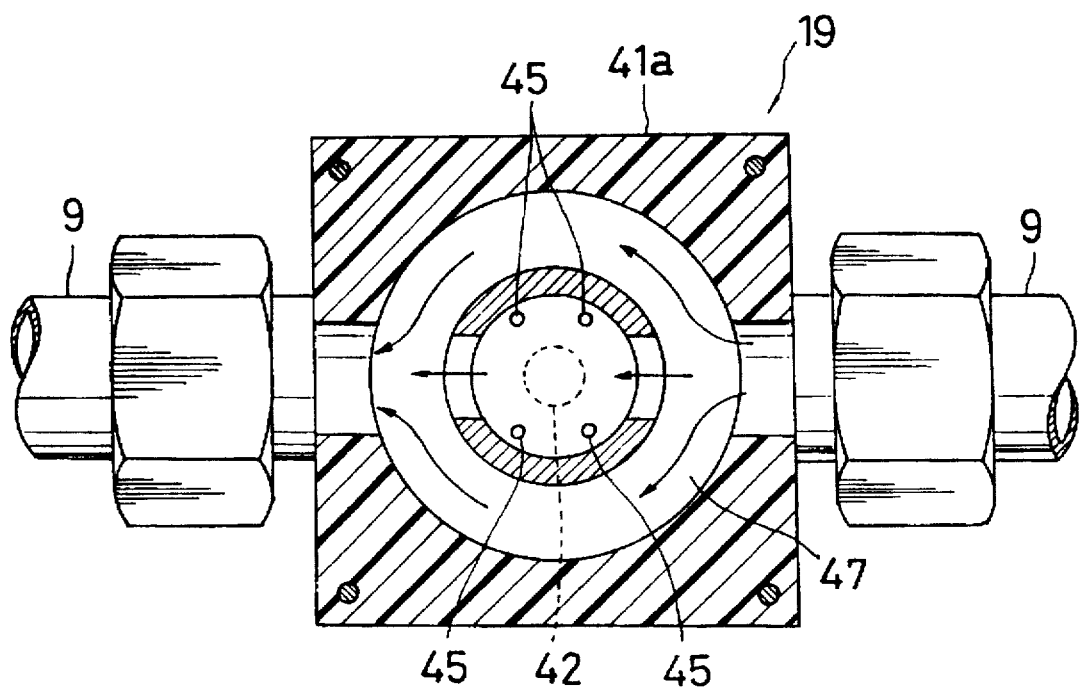
FIG. 12 is a cross section of the flow cell.
Figure 13:
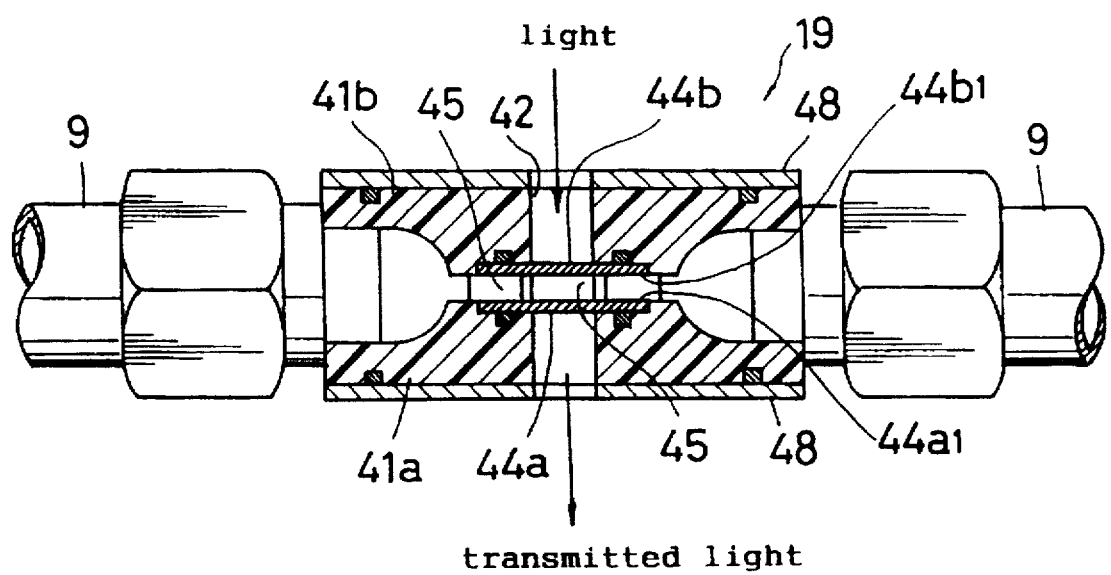
FIG. 13 is a vertical section of the flow cell.

FIG. 11 is an exploded perspective view of the flow cell 19 for measuring transmitted light, embodying the invention. FIG. 12 is a view in cross and FIG. 13 is a view in vertical section of the flow cell.

The transmitted light measuring flow cell (sample flow cell) 19 in this embodiment includes vertically separable frames 41a and 41b connected to the treating solution supply pipe 9 for circulating an object fluid (treating solution) therethrough. The frames 41a and 41b are formed of a fluororesin, for example and define bore 42 centrally thereof for allowing passage of light, respectively. O-rings 43 are mounted around the bores 42 for supporting a pair of light transmitting elements 44a and 44b. These transmitting elements 44a and 44b are formed of a translucent material suited to a wavelength of irradiating light. Particularly where the object fluid contains a highly corrosive chemical such as hydrofluoric acid (HF), a translucent material such as sapphire ($Al_2O_3$) or quartz is employed. Where the object fluid is at a high temperature, in particular, a material having a low coefficient of thermal expansion, such as quartz, is employed.

Coatings 44a1 and 44b1 corrosion-resistant with respect to the object fluid are formed on surfaces of transmitting elements 44a and 44b exposed to the object fluid. Varied materials are available for forming the coatings 44a1 and 44b1 as long as they are corrosion-resistant with respect to the object fluid. A preferred material is a fluororesin which is corrosion-resistant to varied chemicals and has excellent heat resistance as well. This embodiment employs FEP (tetrafluoroethylene-hexafluoropropylene copolymer) film, which is a type of fluororesin, for forming the coatings 44a1 and 44b1. These coatings 44a1 and 44b1 are pressed in place on the transmitting elements 44a and 44b. The FEP film used has a thickness, e.g. approximately 70 μm, for passing light without substantially lowering transmittance.

The light transmitting elements 44a and 44b are protected from corrosion since coatings 44a1 and 44b1 are corrosion-resistant to the object fluid and are formed on the surface thereof exposed to the object fluid. The material forming the transmitting elements 44a and 44b is thereby prevented from dissolving into the object fluid to contaminate same. This serves to stabilize the Cell length over a long period of time. Thus, light intensity is measured in a steady manner over a long period.

In this embodiment, the transmitting elements 44a and 44b are opposed to each other and extend parallel to the axis of flow of the object fluid. Four spacers 45 are interposed between the coating 44a1 on the transmitting element 44a and the coating 44b1 on the transmitting element 44b to maintain the predetermined distance or cell length "d" therebetween. These spacers 45 are formed of FEP as are the coatings 44a1 and 44b1. The spacers 45 have a length, i.e. the cell length, determined according to the light absorbance of the object fluid, which usually is 1 to 3 mm.

The frames 41a and 41b have circulating grooves 47 defined around the transmitting elements 44a and 44b mounted thereon, respectively, for allowing passage of part of the object fluid. The frames 41a and 41b define a passage for the object fluid which passage has cross-sectional area substantially corresponding to that of the supply pipe 9 connected thereto. The frames 41a and 41b are sealed tight by O-rings not shown, and secured to each other by screws as sandwiched between a pair of cover plates 48 having central openings.

With the transmitted light measuring flow cell 19 having the above construction, light of a predetermined wavelength is emitted from the light source 21 to one of the transmitting elements 44b, and a light intensity emerging from the other transmitting element 44a is measured by the optical detector 25 to determine the transmitted light intensity of the object fluid. Since the transmitting elements 44a and 44b are protected from corrosion, the cell length "d" between elements 44a and 44b is invariable with the passage of time, to enable transmitted light intensity to be measured steadily over a long period of time. Thus, the wafer cleaning or treating apparatus employing this transmitted light measuring flow cell 19 can be used for adjusting the concentration of the object fluid (semiconductor cleaning or treating solution) accurately.

The light transmitting elements 44a and 44b may be formed of quartz. Each is a disk that is 20 mm in diameter and is 1.5 mm thick, with varied coatings 44a1 and 44b1 formed on the disk surfaces that would otherwise be exposed to the object fluid. The coating surfaces of transmitting elements 44a and 44b are optically polished. In the above description, one transmitted light measuring flow cell 19 has been discussed. In the following description, a further transmitted light measuring flow cell (reference cell) will be used to discuss the ratio of the transmitted light intensity of the flow cell 19 to that of the reference cell, i.e. transmittance. The irradiating light used includes infrared light IR (wavelength: 2210 nm) and ultraviolet light (wavelength: 290 nm).

The coatings are formed of FEP and PFA (tetrafluoroethylene-perfluoalkylvinlether copolymer)

which are fluororesins. Methods of forming the coatings, taking a spreading process and a pressing process for example will be described.

In a first sample (1), the coatings are formed by spreading PFA in a thickness of 80 to 140 µm. In a second sample (2), the coatings are formed by spreading PFA in a thickness of 15 to 20 µm. In a third sample (3), the coatings are formed by spreading FEP in a thickness of 65 to 85 µm. In a fourth example (4) the coatings are formed of FEP film having a thickness of 70 µm as described hereinbefore. In a normal spreading process for forming the coatings, the surfaces of the transmitting elements are blasted and then primed to improve tightness between the transmitting elements and coatings. In this example, such preparatory processes are omitted to avoid lowering of light transmission. The only exception is sample (4), in which the coatings are formed by pressing and therefore the priming process is carried out. In the spreading process, the coatings should preferably be formed to present uniform surfaces, as otherwise light would be scattered by rough coating surfaces and thereby affect transmittance.

Figure 14:
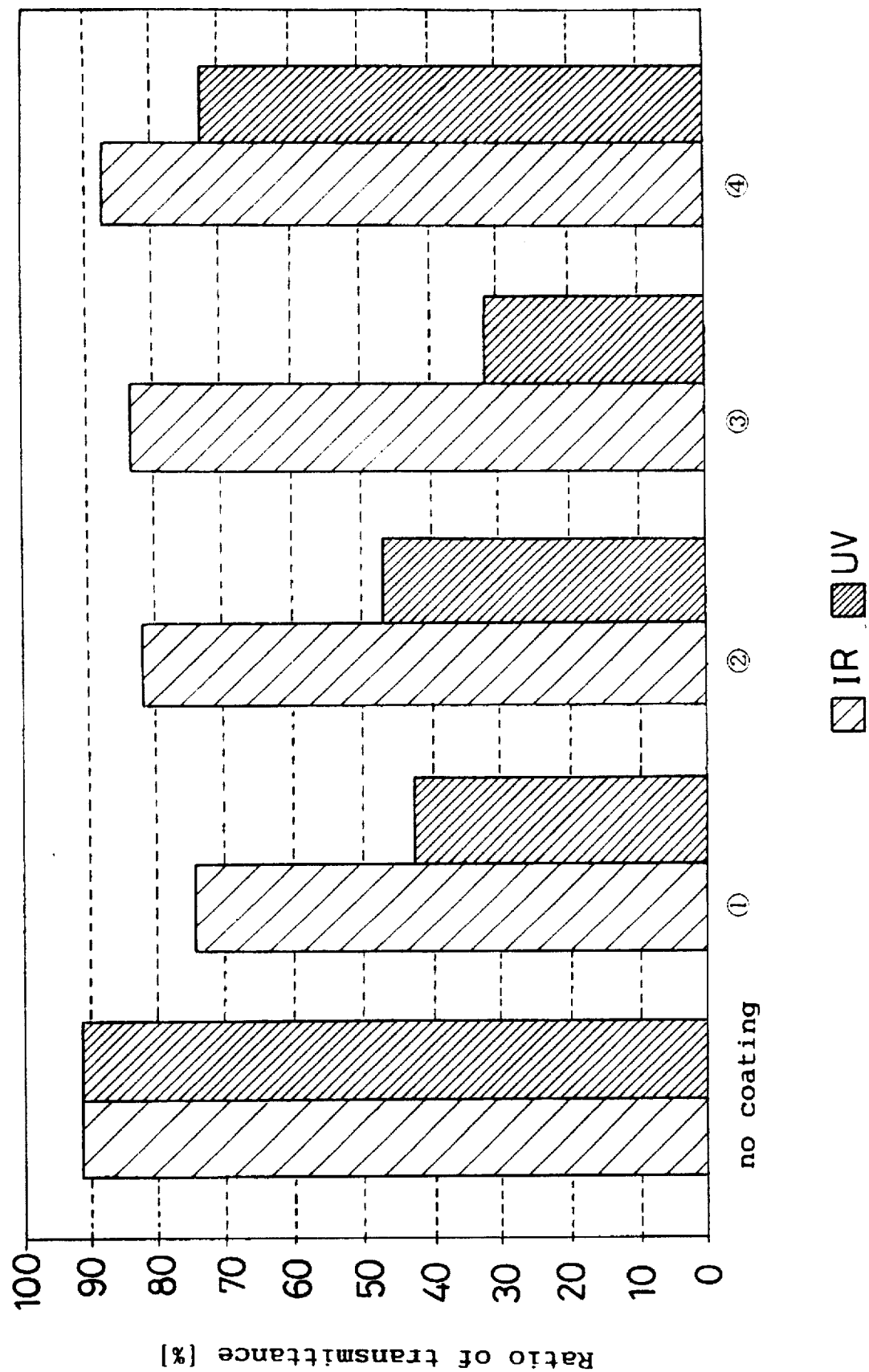
FIG. 14 is the graph for comparing specific transmittance of varied coatings.

As a reference for comparing samples (1) to (4), a transmittance obtained through the transmitted light measuring flow cell 19 without the transmitting elements 44a and 44b is employed. Ratios of transmittance of samples (1) to (4) to the transmittance of this reference are obtained. The ratios of transmittance, each of which is an average value measured to four different elements in respective samples (1) to (4), are shown below along with reference data obtained from the transmitting elements (quartz) without the coatings. FIG. 14 is a graph of these data. Results of Ration of Transmittance Measurement

| samples | infrared light IR | ultraviolet light UV |
| --- | --- | --- |
| no coatings (reference) | 91.6% | 91.4& |
| sample (1) | 74.4% | 43.0% |
| sample (2) | 82.3% | 47.4% |
| sample (3) | 84.0% | 32.6% |
| sample (4) | 88.3% | 73.4% |

As seen from the above measurement results, sample (4) has high ratio of transmittance both for infrared light IR and ultraviolet light UV. Thus, FEP film is a preferred material for forming the coatings, and the pressing process is a preferred method for forming the coatings. These materials and processes are suited for measurement of the transmitted light intensity and transmittance of an object fluid having high absorbance.

This embodiment has been described, exemplifying FEP and PFA as materials for forming the coatings, but various other types of fluororesin may be employed. These include PTFE (polytetrafluoroethylene), PVdF (polyvinylidene fluoride), PCTFE (polychlorotrifluoro-ethylene), EPE (tetrafluoroethylenehexafluoropropylene-perfluoroalkylvinylether copolymer), ETFE (tetrafluoroethylene-ethylene copolymer), ECTFE (chlorotrifluoroethylene-ethylene copolymer) and PVF (polyvinyl fluoride). Further, various materials other than the above fluororesins, such as polyethylene and polypropylene, may be used for forming the coatings as long as they are corrosion-resistant with respect to the object fluid.

The above embodiment has been described, exemplifying quartz and sapphire for forming the light transmitting elements. However, various other materials may be used as long as they provide a sufficient transmittance with respect to the wavelength of irradiating light.

D. Transmitted Light Measuring Optical System Suited for Use in Substrate Treating Apparatus An optical system for measuring transmitted light suitably used in the apparatus shown in FIGS. 1 and 5 will be described next. This optical system includes the light source 21, light divider 22, sample flow cell 19, reference cell 23 (or optical filter F), optical path switcher 24 and optical detector 25.

Figure 15:
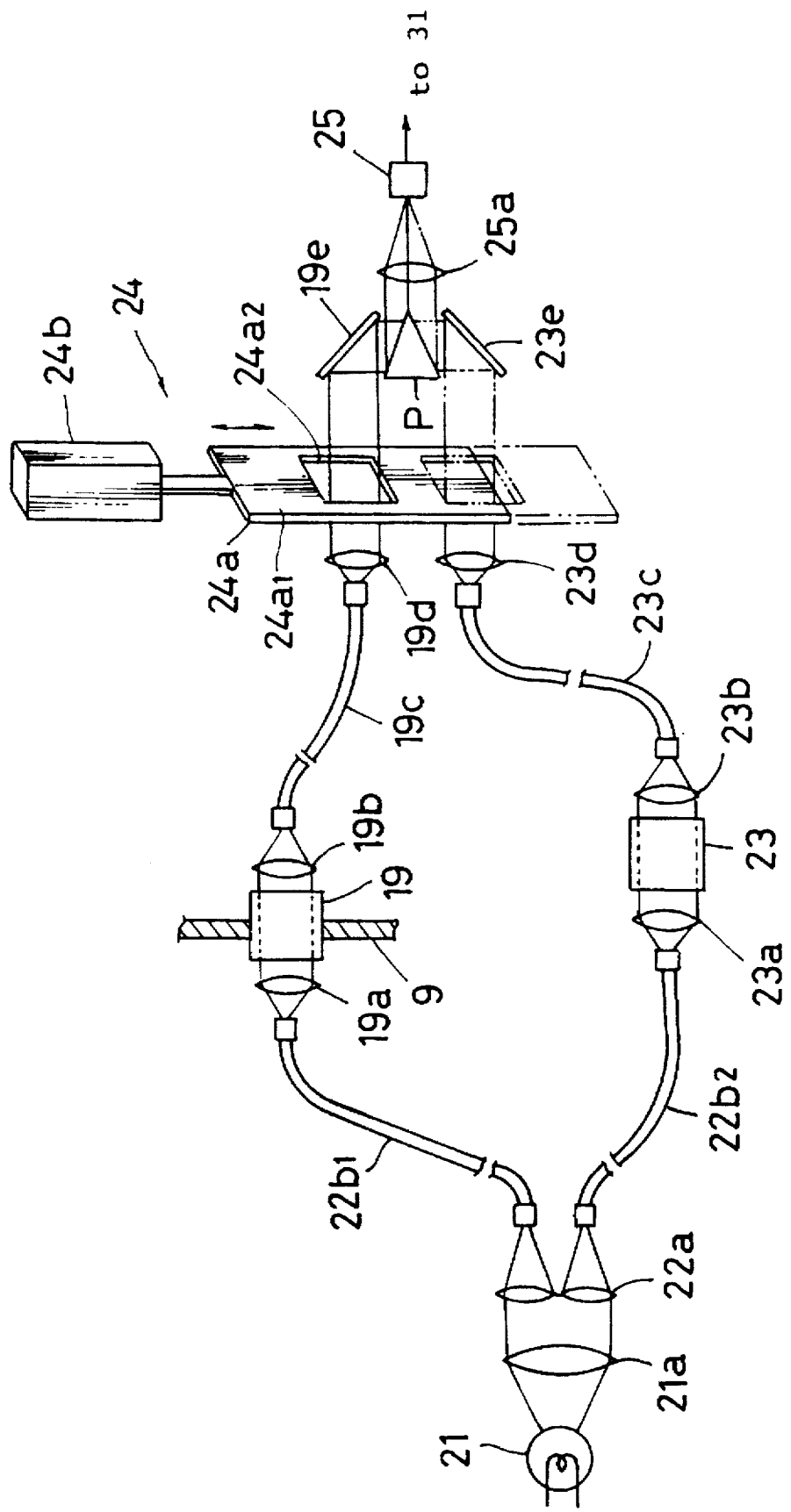
FIG. 15 is a schematic of an optical system for measuring transmitted light.

FIG. 15 is a schematic of the optical system for measuring transmitted light. In this example, the optical system is applied to the apparatus according to the first embodiment. However, the optical system is equally applicable to the apparatus according to the second embodiment.

The light emitted from the light source 21 is converged to parallel rays by a collimator lens 21a to travel to a pair of condenser lenses 22a. One part of light converged by the condenser lens 22a enters an optical fiber $22b_1$, while the other part enters an optical fiber $22b_2$. The light exiting a terminal end of optical fiber $22b_1$ is converged again to parallel rays by a collimator lens 19a to enter the sample flow cell 19. The light transmitted through the sample flow cell 19 is converged by a condenser lens 19b to enter an optical fiber 19c. The light exiting the optical fiber 19c is further converged to parallel rays by a collimator lens 19d.

The other part of light converged by the condenser lens 22a enters the optical fiber $22b2$, converger to parallel rays by a collimator lens 23a to enter the reference cell 23. The light transmitted through the reference cell 23 is converged by a condenser lens 23b to enter an optical fiber 23c. The light exiting the optical fiber 23c is converged to parallel rays by a collimator lens 23d.

The light transmitted through the sample flow cell 19 is reflected 90 degrees by a reflecting mirror 19e opposed to the collimator lens 19d, to enter a prism P. The light transmitted through the reference cell 23 is reflected 90 degrees by a reflecting mirror 23e opposed to the collimator lens 23d, to enter the prism P. The light reflected by the prism P is converged by a condenser lens 25a to enter the optical detector 25.

A light selecting shutter 24a is disposed between collimator lenses 19d, 23d and reflecting mirrors 19e, 23e. This shutter 24a is in the form of a plate including a shielding portion 24a1, and an opening 24a2 acting as a light transmitting portion. The light selecting shutter 24a is reciprocable by an air cylinder 24b as indicated by an arrow in FIG. 15, to direct the parts of light transmitted through the sample flow cell 19 and reference cell 23 alternately to the reflecting mirror 19e and reflecting mirror 23e. The air cylinder 24b acting as the drive device is controllable by the optical path switcher control unit 39 of concentration controller 30, to extend and retract a working rod thereof. The optical path switcher control unit 39, light selecting shutter 24a (shielding portion $24a_1$ and opening $24a_2$) and air cylinder 24b correspond to the optical path switching means of the present invention.

In the optical path switcher 24 having the above construction, the light transmitted through the sample flow cell 19 enters the optical detector 25 when the air cylinder 24b is contracted, and the light transmitted through the reference cell 23 enters the optical detector 25 when the air cylinder 24b is extended.

Figure 16:
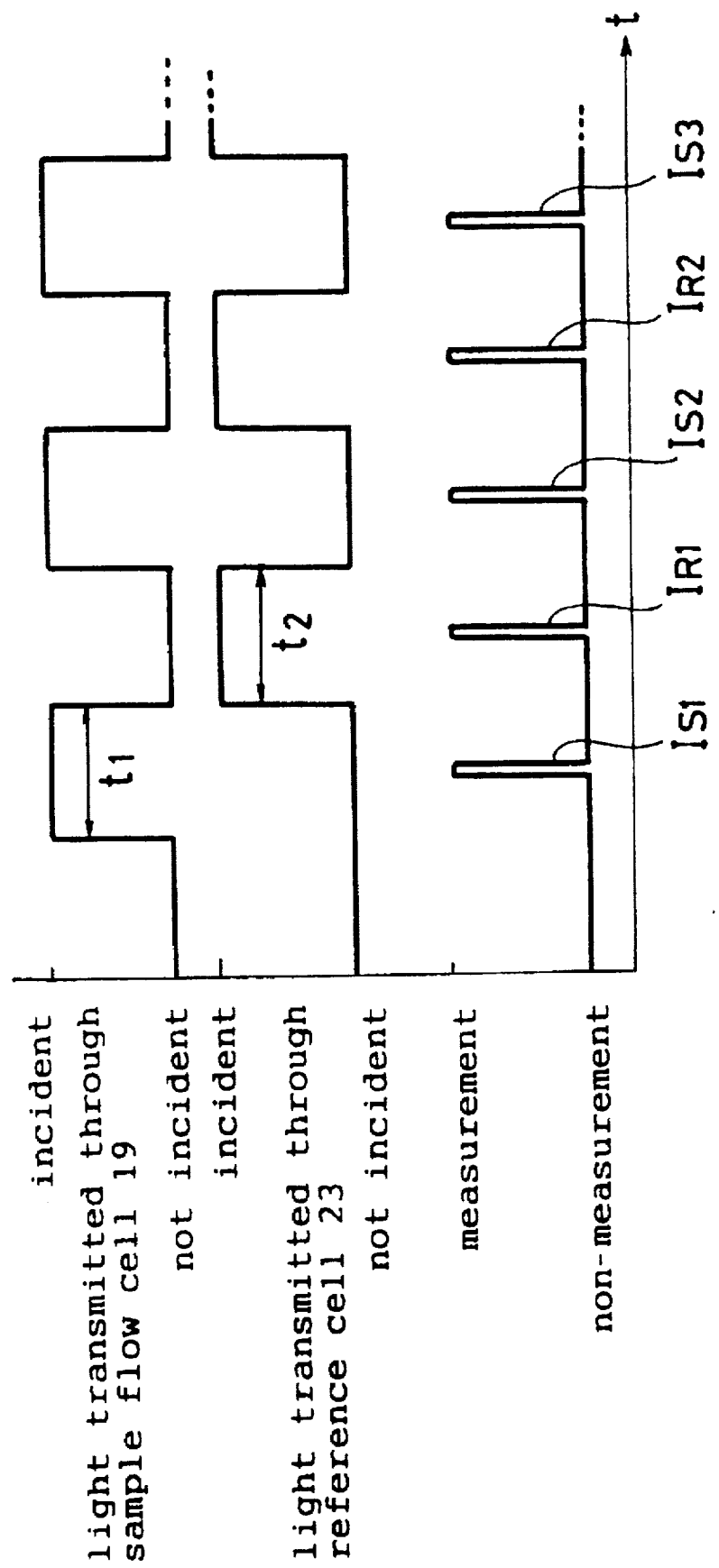
FIG. 16 is a timing chart showing operation of an optical path switcher control unit and measuring timing of a transmitted light intensity measuring unit for use in the optical system shown in FIG. 15.

A concentration adjusting sequence of the substrate treating apparatus employing the above transmitted light measuring optical system will be described next with reference to FIG. 16 which is a timing chart showing operating timing of optical path switcher control unit 39 and measuring timing of transmitted light intensity measuring unit 31.

After using the transmitted light intensity measuring unit 31 to confirm that the treating solution has reached the predetermined temperature, the transmitted light intensity measuring unit 31, the transmitted light intensity measuring unit 31 controls the optical path switcher control unit 39 to drive the light selecting shutter 24a. The switcher control unit 39 contracts the air cylinder 24b for a predetermined time t1, and extends the air cylinder 24b for a predetermined time t2. Consequently, the light transmitted through the sample flow cell 19 is incident on the optical detector 25 for time t1, and the light transmitted through the reference cell 23 is incident on the optical detector 25 for time t2 as shown in FIG. 16. The predetermined time t1, t2 is set to one second, respectively, for example.

The transmitted light intensity measuring unit 31 takes in an output signal of optical detector 25 at an appropriate point during time t1, and outputs the signal as sample transmitted light intensity $I_S$. Further, the measuring unit 31 takes in an output signal of optical detector 25 at an appropriate point during time t2, and measures the signal as a reference transmitted light intensity $I_R$. In this way, the light emitted from one light source 21 is divided to travel through the sample flow cell 19 and reference cell 23. The divided parts of light transmitted through the sample flow cell 19 and reference cell 23 enter one optical detector 25. Any variations occurring in the luminous intensity of light source 21 or in the sensitivity of optical detector 25 influence both the reference transmitted light intensity $I_R$ and sample transmitted light intensity $I_S$. Consequently, the influences of the variations hardly appear in the ratio therebetween, and the concentration of the treating solution is adjusted accurately based on this ratio.

The transmitted light intensity measuring unit 31 repeatedly measures sample transmitted light intensity $I_S$ and reference transmitted light intensity $I_R$, and processes the transmitted light intensities successively measured, as follows. First, the measuring unit 31 determines ratio $T_{11}$ ($=I_{S1}/I_{R1}$) between first sample transmitted light intensity $I_{S1}$ and first reference transmitted light intensity $I_{R1}$, and ratio $T_{21}$ ($=I_{S2}/I_{R1}$) between second sample transmitted light intensity $I_{S2}$ and first reference transmitted light intensity $I_{R1}$, and determines average $T_{AV1}$ thereof. ($T_{AV1}=I_{S2}/I_{R2}$). Next, the measuring unit 31 determines an average $T_{AV2}$ of ratio $T_{21}$ between second sample transmitted light intensity $I_{S2}$ and first reference transmitted light intensity $I_{R1}$, and ratio $T_{22}$ ($=I_{S2}/I_{R2}$) between second sample transmitted light intensity $I_{S2}$ and second reference transmitted light intensity $I_{R2}$. This process is carried out successively to obtain moving averages. Each moving average $T_{AVn}$ is given to the transmittance computing unit 36.

In this way, moving averages are determined of the ratio between sample transmitted light intensity $I_S$ and reference transmitted light intensity $I_R$ which are in a relationship to repeat "smaller" and "greater", compared with an ideal condition where the sample transmitted light intensity $I_S$ and reference transmitted light intensity $I_R$ are measured simultaneously. Thus, ratios between sample transmitted light intensity $I_S$ and reference transmitted light intensity $I_R$ are obtained with high precision and in a near-ideal condition by suppressing the influences of variations in the sensitivity of optical detector 25.

Figure 17:
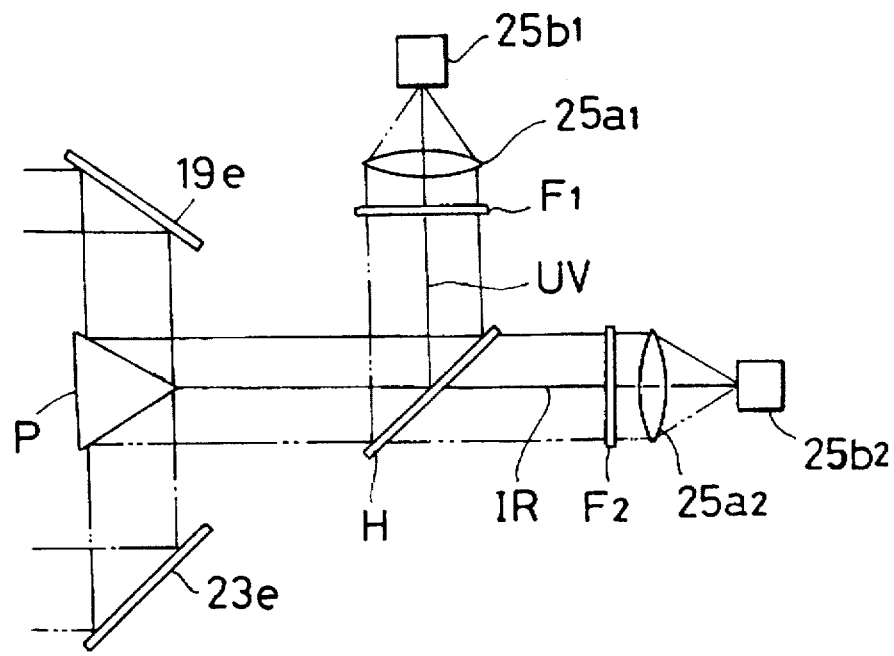
FIG. 17 is a schematic of a modified light detector.

Some types of treating solutions that need to be measured for transmitted light intensities in a plurality of wavelength bands. A treating solution including ammonia and hydrogen peroxide, for example, has wide variations in the transmitted light intensity due to variation of concentration of ammonia in the infrared wavelength band, and wide variations in the transmitted light intensity due to variation of concentration of hydrogen peroxide in the ultraviolet wavelength band. Preferably, therefore, an optical detector 25 as shown in FIG. 17 should be used to measure the transmitted light intensity of such treating solution, and control its concentration based thereon.

Specifically, the light transmitted through the sample flow cell 19 or reference cell 23 enters a prism P. Then, the light is separated by a dichroic mirror H into ultraviolet light UV and visible and infrared light IR. The two types of light travel to an ultraviolet band-pass filter F1 and an infrared band-pass filter F2 for selecting measurement wavelengths of ultraviolet light and infrared light, respectively. Then, the two types of light travel through a condenser lens $25a_1$ and a condenser lens $25a_2$ to an ultraviolet detector $25b_1$ (e.g. a semiconductor device or a photo-electric tube formed of GaP or the like) and an infrared detector $25b_2$ (e.g. a semiconductor device formed of PbS, GaAsP or the like) having spectral sensitivities to the wavelengths selected by the band-pass filters, respectively.

In this construction, sample transmitted light intensities $I_{S(UV)}$ and $I_{S(IR)}$ and reference transmitted light intensities $I_{V(UV)}$ and $I_{V(IR)}$ are measured for the ultraviolet light and infrared light, respectively. Then, as described above, ratio $T_{11(UV)}$ ($=I_{S1(UV)}/I_{R1(UV)}$) between first sample transmitted light intensity $I_{S1(UV)}$ and first reference transmitted light intensity $I_{R1(UV)}$, and ratio $T_{11(IR)}$ ($=I_{S1(IR)}/I_{R1(IR)}$) between first sample transmitted light intensity $I_{S1(IR)}$ and first reference transmitted light intensity $I_{R1(IR)}$, are determined for the ultraviolet light and infrared light, respectively. Such ratios are successively obtained for the ultraviolet light and infrared light, respectively.

Figure 18:
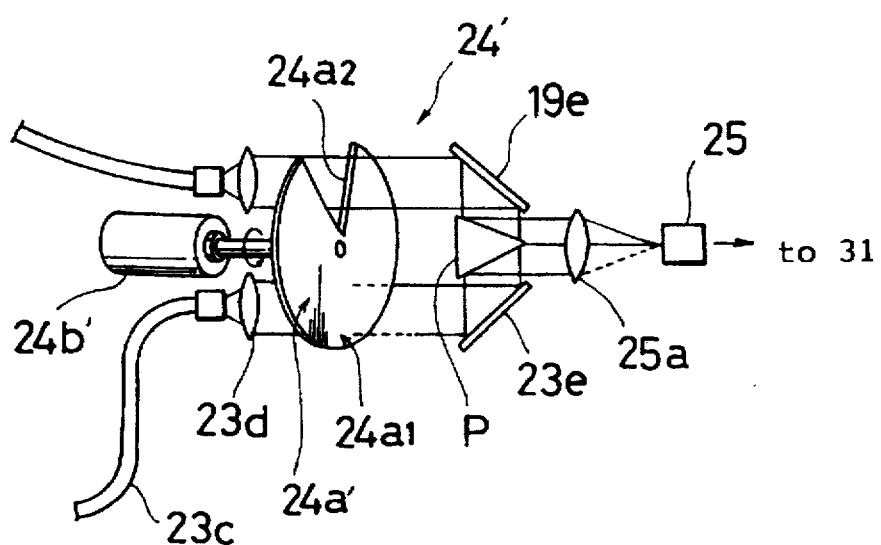
FIG. 18 is a schematic of a modified optical system for measuring transmitted light.

The optical path switcher 24 may be modified as shown in FIG. 18.

Figure 19:
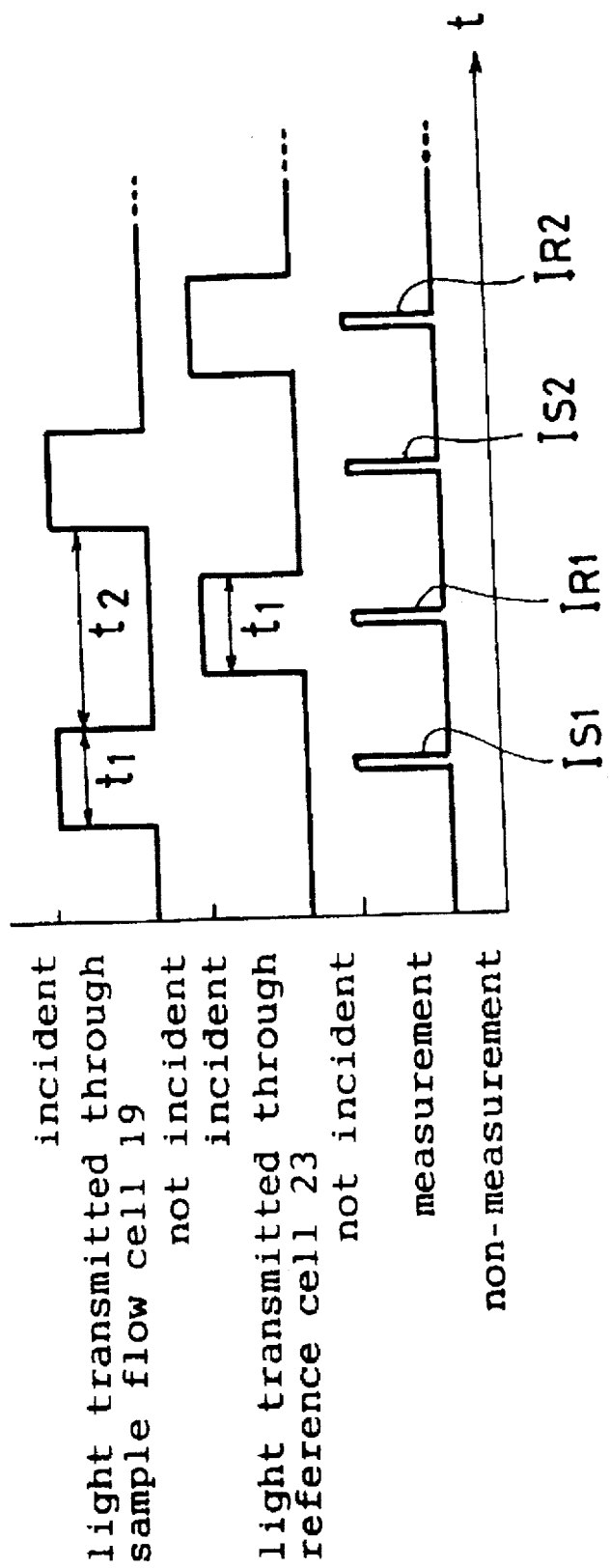
FIG. 19 is a timing chart showing operation of an optical path switcher control unit and measuring timing of a transmitted light intensity measuring unit for use in the modified optical system shown in FIG. 18.

In this example, the light selecting shutter 24a is replaced by a light selecting disk 24a' including a shielding portion $24a_1$, and a cutout portion $24a_2$ having a predetermined ratio to the shielding portion $24a_1$ to act as a light transmitting portion. The air cylinder 24b is replaced by a motor 24b' for rotating the disk 24a' at a predetermined speed. The motor 24' is controlled by the optical path switcher control unit 39 as shown in FIG. 19, for example. In this example, the parts of light transmitted through the sample flow cell 19 and reference cell 23 alternately irradiate the optical detector 25 for time t1, with intervals of time t2 followed by each time t1. The transmitted light intensity measuring unit 31 measures sample transmitted light intensity $I_S$ and reference transmitted light intensity $I_R$ synchronously with the respective irradiation timing. This example provides times (t2–t1) during which the light does not irradiate the optical detector 25. This produces an effect similar to where a chopping sector is provided to suppress heating of the optical detector 25 through intermittent irradiation, thereby enabling a still steadier measurement of transmitted light intensities.

The optical path switcher 24 may be disposed in any location between the light divider 22 and optical detector 25. For example, the optical path switcher 24 may be disposed close to the light source 21, between the collimator lens 21a and condenser lens 22a (see FIG. 15). In this case, the optical fibers 19c and 23c, preferably, have cores and clads joined together at the same ends to form a multi-core bundle, bifurcated optical fiber, so that the two parts of light exit the joined ends. With this construction, the parts of light transmitted through the sample flow cell 19 and reference cell 23 are converged by this optical fiber. The optical detector 25 need not be constructed to converge the two transmitted parts of light.

The technique of obtaining the sample transmitted light intensity ratio and the like by moving averages as described hereinbefore is applicable also to the substrate treating apparatus shown in FIG. 9. When the flow control valve V2 in FIG. 9 is opened, for example, the chemical from the chemical tank $5_1$ mixes into deionized water to form a treating solution flowing through the treating solution supply pipe 9'. Based on fluid information applied, the transmitted light intensity measuring unit 31 determines the fluid circulating through the sample flow cell 19 to be the treating solution (sample fluid). Then, the measuring unit 31 repeatedly measures output signals from the optical detector 25 at suitable intervals as sample transmitted light intensity $I_S$. The resulting data are processed as follows.

The measuring unit 31 determines ratio $T_1$ ($=I_{S1}/I_R$) between first sample transmitted light intensity $I_{S1}$ and reference transmitted light intensity $I_R$, and ratio $T_2$ ($=I_{S2}/I_R$) between second sample transmitted light intensity $I_{S2}$ and reference transmitted light intensity $I_R$, and determines average $T_{AV1}$ thereof. Subsequently, the measuring unit 31 determines an average $T_{AV2}$ of ratio $T_2$ between second sample transmitted light intensity $I_{S2}$ and reference transmitted light intensity $I_R$, and ratio $T_3$ between third sample transmitted light intensity $I_{S3}$ and reference transmitted light intensity $I_R$. This process is carried out successively to obtain moving averages. Each moving average $T_{AVn}$ is given to the transmittance computing unit 36.

In the second embodiment shown in FIG. 5, the standard transmitted light intensity ratio, reference transmitted light intensity and sample transmitted light intensity may be determined by the above moving average method. This is achieved by detecting the transmitted light intensities and reduced source transmitted light intensities repeatedly to determine the ratios between standard, reference and sample transmitted light intensities, and the corresponding reduced source light intensities.

The present invention may be embodied in other specific forms without departing from the spirit or essential attributes thereof and, accordingly, reference should be made to the appended claims, rather than to the foregoing specification, as indicating the scope of the invention.

What is claimed is:

1. A concentration controlling method for controlling a concentration of a treating solution for use in treatment of substrates, based on a transmitted light intensity of the treating solution measured with first transmitted light intensity measuring means, and a transmitted light intensity of a solvent forming part of the treating solution measured with second transmitted light intensity measuring means, said method comprising a standard setting process including steps of:

(a) measuring transmitted light intensities of only said solvent with said first transmitted light intensity measuring means, while varying temperature of said solvent, and storing calibration curve data showing a relationship between the temperatures and transmitted light intensities of said solvent;

(b) measuring a transmitted light intensity of a standard treating solution prepared at a predetermined concentration and temperature in advance, as a standard transmitted light intensity, with said first transmitted light intensity measuring means;

(c) measuring a transmitted light intensity of said solvent with said second transmitted light intensity measuring means, as a reference transmitted light intensity;

(d) computing, based on said temperature of said standard treating solution and said calibration curve data stored, an estimated transmitted light intensity corresponding to a transmitted light intensity of said solvent to be measured with said second transmitted light intensity measuring means when said solvent is adjusted to the same temperature as that of said standard treating solution, and computing a correction factor based on a ratio between said reference transmitted light intensity and said estimated transmitted light intensity; and (e) computing a transmittance of said standard treating solution at said predetermined temperature, as a standard transmittance, from said standard transmitted light intensity, said reference transmitted light intensity and said correction factor; and said method also comprising a feedback control process including steps of:

(f) measuring the transmitted light intensity of said treating solution for actual use in treatment of substrates, as a sample transmitted light intensity, with said first transmitted light intensity measuring means;

(g) computing a transmittance of said treating solution, as a sample transmittance, from said sample transmitted light intensity, said reference transmitted light intensity and said correction factor; and (h) controlling the concentration of said treating solution for actual use in treatment of substrate, based on said standard transmittance and said sample transmittance;

said feedback control process being repeated to bring said standard transmittance and said sample transmittance into agreement.

2. A concentration controlling method as defined in claim 1, wherein said step (c) is executed again before or after said step (f) to measure a new reference transmitted light intensity, and step (g) is executed after said deriving said correction factor from a ratio between said new reference transmitted light intensity and said estimated transmitted light intensity.

3. A concentration controlling method as defined in claim 1, wherein said step (a) is executed to measure source-related transmitted light intensities, relating to intensities of light emitted by a light source included in said first and second transmitted light intensity measuring means, at varied temperatures as well as the transmitted light intensities at the varied temperatures, and to store ratios between said transmitted light intensities and said source-related transmitted light intensities (i.e. transmitted light intensity ratios) as said calibration curve data, said steps (b), (c) and (f) being executed to measure said source-related transmitted light intensities as well as said transmitted light intensities to determine ratios therebetween, and to carry out computations based on said ratios.

4. A substrate treating apparatus for treating substrates with a treating solution adjusted to a predetermined concentration and temperature, comprising:

substrate holding means for holding said substrate to be treated;

treating solution storage means for storing said treating solution for treating said substrate held by said substrate holding means;

chemical supply means for supplying a chemical forming part of said treating solution to said treating solution storage means;

solvent supply means for supplying a solvent included in said treating solution to said treating solution storage means;

treating solution supply means for supplying said treating solution stored in said treating solution storage means to said substrate held by said substrate holding means;

first and second sampling means for sampling an object to be measured said having optical paths of the same length, respectively;

first transmitted light intensity measuring means for measuring, with said first sampling means, a standard transmitted light intensity of a standard treating solution prepared at said predetermined concentration and temperature in advance, and for measuring a sample transmitted light intensity of a treating solution for actual use in treatment of substrate, with said first transmitted light intensity measuring means;

second transmitted light intensity measuring means for measuring a transmitted light intensity (reference transmitted light intensity) of said solvent with said second sampling means;

calibration curve data collecting means for measuring transmitted light intensities of only said solvent with said first sampling means, while varying temperature of said solvent, and collecting calibration curve data showing relationship between the temperatures and transmitted light intensities of said solvent;

correction factor computing means for computing, based on said temperature of said standard treating solution and said calibration curve data collected, an estimated transmitted light intensity corresponding to a transmitted light intensity of said solvent measured with said second sampling means and said second transmitted light intensity measuring means when said solvent is adjusted to the same temperature as said standard treating solution, and computing a correction factor from a ratio between said reference transmitted light intensity and said estimated transmitted light intensity;

standard transmittance computing means for computing a transmittance of said standard treating solution at said predetermined temperature, as a standard transmittance, based on said standard transmitted light intensity, said reference transmitted light intensity and said correction factor;

sample transmittance computing means for computing a transmittance of said treating solution, as a sample transmittance, based on said sample transmitted light intensity, said reference transmitted light intensity and said correction factor; and concentration control means for controlling the concentration of said treating solution for actual use in treatment of substrate, by controlling said chemical supply means and said solvent supply means based on said standard transmittance and said sample transmittance.

5. A substrate treating apparatus as defined in claim 4, wherein said concentration control means includes feedback control means for controlling said chemical supply means and said solvent supply means based on a difference between said standard transmittance and said sample transmittance.

6. A substrate treating apparatus as defined in claim 4, wherein at least said first sampling means is a transmitted light measuring flow cell having an opposed pair of light transmitting elements formed of a translucent material and spaced from each other by a predetermined distance, light entering said flow cell through one of said light transmitting elements to irradiate an object flowing between said transmitting elements, a light intensity emerging through the other light transmitting element to be measured, said flow cell having coatings that are corrosion-resistant with respect to said object fluid and formed on surfaces of said light transmitting elements exposed to said object fluid.

7. A substrate treating apparatus as defined in claim 6, wherein said coatings are formed of a fluororesin.

8. A substrate treating apparatus as defined in claim 4, wherein said first and second transmitted light intensity measuring means include a single common light source, light dividing means for dividing light emitted from said light source for said first and second sampling means, a single optical detector for receiving divided parts of light transmitted through said first and second sampling means, and outputting signals corresponding to intensities of said divided parts of light, respectively, and optical path switching means for alternately causing said divided parts of light to enter said optical path switching means, said signals being accepted from said optical detector synchronously with switching action of said optical path switching means, such that an output signal of said optical detector accepted when said optical detector receives light transmitted through said second sampling means is measured as said reference transmitted light intensity, and an output signal of said optical detector accepted when said optical detector receives light transmitted through said first sampling means is measured as said standard transmitted light intensity.

9. A substrate treating apparatus as defined in claim 8, wherein said optical path switching means includes a light shielding shutter with a plate having a light transmitting portion and a light shielding portion formed in a predetermined ratio, and drive means for driving said light shielding shutter for alternately allowing the light transmitted through said second sampling means and the light transmitted through said first sampling means to irradiate said optical detector.

10. A substrate treating apparatus as defined in claim 8, wherein said first and second transmitted light intensity measuring means are operable to repeat measurement of said standard transmitted light intensity and said sample transmitted light intensity, and measurement of said reference transmitted light intensity, and to compute moving averages of ratios between transmitted light intensities and reference transmitted light intensities adjacent each other in time, i.e. a ratio between an (i)th ("i" being a natural number) transmitted light intensity and an (i)th reference transmitted light intensity, a ratio between an (i+1)th transmitted light intensity and the (i)th reference transmitted light intensity, and a ratio between the (i+1)th transmitted light intensity and the (i+1)th reference transmitted light intensity.

11. A concentration controlling method for controlling a concentration of a treating solution for use in treatment of substrates, based on a transmitted light intensity of the treating solution and a transmitted light intensity of a solvent included in the treating solution measured with common transmitted light intensity measuring means, said method comprising a standard setting process including steps of:

(a) measuring transmitted light intensities of only said solvent with said transmitted light intensity measuring means, while varying temperature of said solvent, and storing calibration curve data showing a relationship between the temperatures and transmitted light intensities of said solvent;

(b) measuring a transmitted light intensity of a standard treating solution prepared at a predetermined concentration and temperature in advance, as a standard transmitted light intensity, with said transmitted light intensity measuring means;

(c) measuring a transmitted light intensity of said solvent adjusted at a constant temperature with said transmitted light intensity measuring means, as a reference transmitted light intensity;

(d) computing, based on said temperature of said standard treating solution and said calibration curve data stored, an estimated transmitted light intensity corresponding to a transmitted light intensity of said solvent to be measured with said transmitted light intensity measuring means when said solvent is adjusted to the same temperature as said standard treating solution, and computing a correction factor based on a ratio between said reference transmitted light intensity and said estimated transmitted light intensity; and (e) computing a transmittance of said standard treating solution at said predetermined temperature, as a standard transmittance, based on said standard transmitted light intensity, said reference transmitted light intensity and said correction factor; and said method also comprising a feedback control process including steps of:

(f) measuring the transmitted light intensity of said treating solution for actual use in treatment of substrates with said transmitted light intensity measuring means, as a sample transmitted light intensity;

(g) computing a transmittance of said treating solution, as a sample transmittance, based on said sample transmitted light intensity, said reference transmitted light intensity and said correction factor; and (h) controlling the concentration of said treating solution for actual use in treatment of substrate, based on said standard transmittance and said sample transmittance;

said feedback control process being repeated to bring said standard transmittance and said sample transmittance into agreement.

12. A concentration controlling method as defined in claim 11, wherein said step (c) is executed again before said step (f) to measure a new reference transmitted light intensity, and said step (g) is executed after deriving said correction factor from a ratio between said new reference transmitted light intensity and said estimated transmitted light intensity.

13. A concentration controlling method as defined in claim 11, wherein said step (a) is executed to measure source-related transmitted light intensities, relating to intensities of light emitted by a light source included in said transmitted light measuring means at varied temperatures as well as the transmitted light intensities at the varied temperatures, and to store ratios between said transmitted light intensities and said source-related transmitted light intensities as said calibration curve data, said steps (b), (c) and (f) being executed to measure said source-related transmitted light intensities as well as said transmitted light intensities to determine ratios therebetween, and to carry out computations based on said ratios.

14. A substrate treating apparatus for treating substrates with a treating solution adjusted to a predetermined concentration and temperature, comprising:

substrate holding means for holding substrates to be treated;

treating solution storage means for storing said treating solution for treating said substrate held by said substrate holding means;

chemical supply means for supplying a chemical for forming part of said treating solution to said treating solution storage means;

solvent supply means for supplying a solvent included in said treating solution to said treating solution storage means;

treating solution supply means for supplying said treating solution stored in said treating solution storage means to said substrate held by said substrate holding means;

sampling means, having a light transmitting portion through which light incident thereon is transmitted, for separately sampling said treating solution and said solvent;

light emitting means for emitting light toward said light transmitting portion of said sampling means;

light receiving means for receiving light transmitted through said light transmitting portion of said sampling means to measure intensity of light transmitted therethrough;

light detecting means for detecting intensity of light emitted by said light emitting means;

transmitted light intensity ratio determining means, using said sampling means, said light emitting means, said light receiving means and said light detecting means, for determining a standard transmitted light intensity ratio between a transmitted light intensity of a standard treating solution prepared at said predetermined concentration and temperature, and intensity of light detected by said light detecting means, for determining a reference transmitted light intensity ratio between a reference transmitted light intensity representing an intensity of light transmitted through only said solvent and intensity of light detected by said light detecting means, and for determining a sample transmitted light intensity ratio between a sample transmitted light intensity representing an intensity of light transmitted through a treating solution for actual use in treatment of substrate and intensity of light detected by said light detecting means;

calibration curve data collecting means for measuring transmitted light intensities of only said solvent, using said light emitting means, said light receiving means, and said sampling means, while varying temperature of said solvent, and collecting calibration curve data showing relationship between the temperatures and transmitted light intensities of said solvent;

correction factor computing means for computing, based on said temperature of said standard treating solution and said calibration curve data collected, a ratio between an estimated transmitted light intensity ratio corresponding to a transmitted light intensity of said solvent measured with said sampling means when said solvent is adjusted to the same temperature as said standard treating solution, and the intensity of light emitted from said light emitting means, as an estimated transmitted light intensity ratio, and computing a correction factor based on a ratio between said reference transmitted light intensity ratio and said estimated transmitted light intensity ratio;

standard transmittance computing means for computing a transmittance of said standard treating solution at said predetermined temperature, as a standard transmittance, based on said standard transmitted light intensity ratio, said reference transmitted light intensity ratio and said correction factor;

sample transmittance computing means for computing a transmittance of said treating solution, as a sample transmittance, based on said sample transmitted light intensity ratio, said reference transmitted light intensity ratio and said correction factor; and concentration control means for controlling the concentration of said treating solution for actual use in treatment of substrate, by controlling said chemical supply means and said solvent supply means based on said standard transmittance and said sample transmittance.

15. A substrate treating apparatus as defined in claim 14, wherein said concentration control means includes feedback control means for controlling said chemical supply means and said solvent supply means based on a difference between said standard transmittance and said sample transmittance.

16. A substrate treating apparatus as defined in claim 14, wherein at least said sampling means includes a transmitted light measuring flow cell having an opposed pair of light transmitting elements formed of a translucent material and spaced from each other by a predetermined distance (cell length), light entering said flow cell through one of said light transmitting elements to irradiate an object fluid flowing between said transmitting elements, a light intensity emerging through the other light transmitting element to be measured, said flow cell having coatings corrosion-resistant with respect to said object fluid and formed on surfaces of said light transmitting elements exposed to said object fluid.

17. A substrate treating apparatus as defined in claim 16, wherein said coatings are formed of a fluororesin.

18. A substrate treating apparatus as defined in claim 14, wherein said light emitting means includes a single light source, an optical filter having a predetermined reduction ratio, light dividing means for dividing light emitted from said light source for said sampling means and said optical filter, and wherein said light receiving means includes a single optical detector for receiving divided parts of light transmitted through said sampling means and said optical filter, and outputting signals corresponding to intensities of said divided parts of light, respectively, and optical path switching means for alternately causing said divided parts of light to enter said optical path switching means, said signals being accepted from said optical detector synchronously with switching action of said optical path switching means, such that an output signal of said optical detector accepted when said optical detector receives light transmitted through said sampling means is measured as one of said standard transmitted light intensity, said reference transmitted light intensity and said sample transmitted light intensity, and an output signal of said optical detector accepted when said optical detector receives light transmitted through said optical filter is measured as an intensity of light (source-related light intensity) emitted from said light emitting means.

19. A substrate treating apparatus as defined in claim 18, wherein said optical path switching means includes a light selecting shutter comprising a plate having a light transmitting portion and a light shielding portion formed in a predetermined ratio, and drive means for driving said light shielding shutter for alternately allowing the light transmitted through said sampling means and the light transmitted through said optical filter to irradiate said optical detector.

20. A substrate treating apparatus as defined in claim 18, wherein said transmitted light intensity measuring means is operable to repeat measurement of said standard transmitted light intensity, said reference transmitted light intensity and said sample transmitted light intensity, and measurement of said source-related light intensity, and to compute moving averages of ratios between transmitted light intensities and source-related light intensities adjacent each other in time, i.e. a ratio between an (i)th ("i" being a natural number) transmitted light intensity and an (i)th source-related light intensity, a ratio between an (i+1)th transmitted light intensity and the (i)th source-related light intensity, and a ratio between the (i+1)th transmitted light intensity and the (i+1)th source-related light intensity, said moving averages being used as a standard transmitted light intensity ratio, a reference transmitted light intensity ratio and a sample transmitted light intensity ratio.

21. A substrate treating apparatus as defined in claim 4, wherein said chemical supply means supplies said chemical in gaseous form.

22. A substrate treating apparatus as defined in claim 14, wherein said chemical supply means supplies said chemical in gaseous form.

* * * * *